(12) United States Patent
Thakur et al.

(10) Patent No.: US 11,504,340 B2
(45) Date of Patent: Nov. 22, 2022

(54) OCULAR COMPOSITIONS

(71) Applicant: THE QUEEN'S UNIVERSITY OF BELFAST, Belfast (GB)

(72) Inventors: Raghu Raj Singh Thakur, Belfast (GB); David Jones, Belfast (GB); Rahul Sonawane, Belfast (GB)

(73) Assignee: THE QUEEN'S UNIVERSITY OF BELFAST, Belfast (GB)

( * ) Notice: Subject to any disclaimer, the term of this patent is extended or adjusted under 35 U.S.C. 154(b) by 0 days.

(21) Appl. No.: 16/612,181

(22) PCT Filed: May 10, 2018

(86) PCT No.: PCT/EP2018/062181
§ 371 (c)(1),
(2) Date: Nov. 8, 2019

(87) PCT Pub. No.: WO2018/206749
PCT Pub. Date: Nov. 15, 2018

(65) Prior Publication Data
US 2021/0378979 A1    Dec. 9, 2021

(30) Foreign Application Priority Data

May 10, 2017    (GB) .................................... 1707462

(51) Int. Cl.
*A61K 9/00* (2006.01)
*B82Y 5/00* (2011.01)
(Continued)

(52) U.S. Cl.
CPC .......... *A61K 9/5192* (2013.01); *A61K 9/0051* (2013.01); *A61K 9/5026* (2013.01);
(Continued)

(58) Field of Classification Search
CPC ............... A61L 27/26; A61L 2300/622; A61L 2300/624; A61L 2430/16; A61L 27/54;
(Continued)

(56) References Cited

U.S. PATENT DOCUMENTS

2018/0325812 A1* 11/2018  Thakur ................ A61K 9/5153

FOREIGN PATENT DOCUMENTS

| EP | 2481399 | 8/2012 |
|---|---|---|
| WO | 2007084418 | 7/2007 |
| WO | 2017081154 | 5/2017 |

OTHER PUBLICATIONS

Cam et al. (Expert Opinion on Drug Delivery 2019;16(9):895-901) (Year: 2019).*

(Continued)

*Primary Examiner* — Ernst V Arnold
(74) *Attorney, Agent, or Firm* — Hovey Williams LLP

(57) ABSTRACT

The invention provides methods of making microparticle and nanoparticle ocular implants from a compositions comprising: 99 to 60% (w/w) of a photopolymerizable composition selected from the group of fragments or monomers consisting of polyalkylene glycol diacrylate and polyalkylene glycol dimethacrylate, wherein the photopolymerizable composition has a molecular weight in the range of 100 to 20,000 Dalton; a biodegradable polymer selected from the group consisting of aliphatic polyester-based polyurethanes, polylactides, polycaprolactones, polyorthoesters and mixtures, copolymers, and block copolymers thereof; a photoinitiator; and a therapeutic agent.

21 Claims, 7 Drawing Sheets

(51) Int. Cl.
*B82Y 40/00* (2011.01)
*A61K 9/51* (2006.01)
*A61K 9/50* (2006.01)
*A61K 45/06* (2006.01)
*B82Y 30/00* (2011.01)

(52) U.S. Cl.
CPC .......... *A61K 9/5031* (2013.01); *A61K 9/5089* (2013.01); *A61K 9/5138* (2013.01); *A61K 9/5146* (2013.01); *A61K 45/06* (2013.01); *B82Y 5/00* (2013.01); *B82Y 30/00* (2013.01); *B82Y 40/00* (2013.01)

(58) Field of Classification Search
CPC ....... C08L 67/04; A61K 45/06; A61K 9/0024; A61K 9/0048; A61K 9/0051; A61K 9/5026; A61K 9/5031; A61K 9/5089; A61K 9/5138; A61K 9/5146; A61K 9/5192; B82Y 30/00; B82Y 40/00; B82Y 5/00

See application file for complete search history.

(56) References Cited

OTHER PUBLICATIONS

Naik et al. (Int J Pharm Bio Sci 2012;3(4):573-590). (Year: 2012).*
Lu Changhai et al, "Hydrogel containing silica shell cross-linked micelles for ocular drug delivery", Journal of Pharmaceutical Sciences, Feb. 1, 2013, vol. 102, No. 2, p. 627-637.
The International Search Report and Written Opinion dated Jul. 19, 2018, issued in PCT/EP2018/062181, filed May 10, 2018.

* cited by examiner

OCULAR COMPOSITIONS

RELATED APPLICATIONS

This application is the U.S. National Stage of International Patent Application No. PCT/EP2018/062181, filed May 10, 2019, which is hereby incorporated by reference in its entirety, and which claims priority to United Kingdom Patent Application No. 1707462.6, filed May 10, 2017.

Loss of sight has a major personal impact on people's daily lives and has a profound economic impact on individuals, families, support agencies, society and the state. Eye diseases such as age age-related macular degeneration (AMD), diabetic retinopathy, glaucoma and ocular inflammations (e.g., uveitis) causes majority of blindness. For example, glaucoma is the considered to be the second leading cause of blindness that affects more than 60 million worldwide. However, daily application of high drug doses (e.g., topical eye drops), due to poor ocular bioavailability, leads to other long-term side effects (e.g., allergy and intolerance to medications), have negative effects on patient compliance, which leads to disease progression from sub-optimal to poor medical management. Importantly, less than 5% of the drug penetration occurs following topical administration that too for only small molecules, resulting in excessive waste of costly drugs, exposure to high drug levels yet poor efficacy/compliance and minimal benefit to the patient.

There is a need for new and improved systems for ocular delivery of therapeutic agents.

Co-pending PCT Application PCT/EP2016/077269 provides ocular compositions that can be administered to the eye in various forms to achieve controlled release of a therapeutic agent (or drug) allowing the flexibility to administer a range of small and large drug molecules including proteins, peptides and gene therapeutics, and maintain their activity for a controlled period of time. The application also provides methods of treating a number of eye diseases comprising administering the ocular compositions of the invention to a subject in need thereof.

There is a need for new and improved methods of making nano and micro particle ocular implants for ocular delivery of therapeutic agents.

SUMMARY OF THE INVENTION

The present invention provides a method of making a nanoparticle or microparticle ocular implant comprising
a) 99 to 60% (w/w) of a photopolymerizable composition selected from the group consisting of fragments or monomers of polyalkylene glycol diacrylate and polyalkylene glycol dimethacrylate, wherein the photopolymerizable composition has a molecular weight in the range of 100 to 20,000 Daltons;
b) a biodegradable polymer selected from the group consisting of lactide/glycolide co-polymer (PLGA), polylactic acid (PLA), polyglycolic acid (PGA), polycaprolactone (PCL), lactide/caprolactone copolymer (PLC), poly (L-lactide) (PLLA) and mixtures, copolymers, and block copolymers thereof;
c) a photoinitiator; and
d) a therapeutic agent,
the method comprising the steps of:
I) mixing the therapeutic agent, the photopolymerizable composition, and the biodegradable polymer, to form mixture i);
II) adding the photoinitiator to form mixture ii);
III) irradiating the mixture ii) with light at a wavelength of between 230 to 550 nm, between 300 to 525 nm, or between 350 to 490 nm for between 1 second and 60 minutes; and
IV) processing the irradiated mixture ii) to obtain microparticles.

Preferably the photopolymerizable polymer is PEGDA and the biodegradable polymer is PLGA.

In one embodiment the mixture ii) is cast as a film prior to irradiation and the step of processing the irradiated mixture includes milling the irradiated film to obtain particles.

The mixture i) is stirred for a time period based on content of biodegradable polymer.

The time period can be typically from 2 minutes to 48 hours.

In the absence of a co-solvent the time period may be from 12 to 48 hours. This period is decreased in the presence of a co-solvent.

Typically mixture i) is vortexed for 2 to 5 minute when a solvent chosen from the dichloromethane, methanol, acetone or mixture of dichloromethane:methanol is used as co-solvents.

Typically, mixture i) is stirred at 100 to 300 rpm speed based on ratio of biodegradable polymer to photopolymerizable polymer.

Typically, the mixture is stirred at room temperature.

Preferably the photoinitiator is dissolved in minimum amount of solvent and added to drug-polymer mixture just before starting the UV exposure.

Preferably, the solvent is acetone or absolute alcohol or methanol.

Preferably mixture ii) is cast as a thin film.

Typically, the thin film has a thickness of 0.2 to 1 mm based on total amount of mixture ii) and diameter of flat surface used. Mixture ii) can be cast on a release liner.

Typically, the film is exposed to UV light for 48 to 300 sec. at 93 to 100% intensity of UV lamp.

The formed films are typically ground in a ball mill or freeze mill using liquid nitrogen.

The polymer film may be initially crushed using mortar-pestle and then introduced in sample cells along with stainless steel balls. The sample cells may be cooled by immersing in liquid nitrogen and then loaded into the mill.

In one particular non-limiting example, a ball mill was operated for 3 min at 25 Hz frequency followed by cooling in liquid nitrogen for 10 min and again operated for 3 min. The cycle was repeated 5 times.

The process can be scaled up using high-capacity freezer mill with operating frequency between 15-25 Hz for 2 to 5 min at each run. The freezing and milling cycle can be repeated 5 to 10 times depending upon frequency used and run time.

The microparticles obtained can be sieved and separated into different sizes and size ranges as required.

In an alternative embodiment the mixture ii) is homogenised at high speed prior to irradiation and the particles are obtained by solvent extraction post irradiation.

Preferably, the mixture i) contains between 5 to 30% w/w of PLGA polymer and between 93.5 to 64% w/w photopolymerizable polymer (PEGDA) of total drug and excipient content.

Preferably, the mixture i) is dissolved in 0.2 to 2 ml acetone or dichloromethane or mixture of dichloromethane and methanol (9:1).

Preferably, the mixture ii) contains 1 to 5% w/w therapeutic agent (like Dexamethasone) and between 0.1 to 1% w/v photo initiator (Irgacure) of total solid content.

Typically an emulsion is formed when mixture ii) added to 0.15 to 2% w/v polyvinyl alcohol (PVA) aqueous solution with homogenization at speed between 6000 to 18000 rpm for between 1 to 4 min to reduce size to micro or nanometer range.

Alternatively, the emulsion can also be prepared by adding mixture i) into 0.01 to 0.5% w/v d-α-tocopheryl polyethylene glycol 1000 succinate (vitamin E TPGS or TPGS) or 0.1 to 2% w/v polysorbate 80 (Tween 80) or 0.1 to 1% w/v Poloxamer 188 when used as emulsifiers.

The above formed emulsion is further added to between 5 to 20 mL of 50 to 500 mM sodium sulfate solution with homogenization at speed between 6000 to 18000 rpm for between 1 to 4 min to reduce size to micro or nanometer range. The addition of emulsion in sodium sulfate solution help in precipitation of PEGDA on the surface PLGA particles as a coating.

The emulsion is typically stirred at 100 to 400 rpm and simultaneously exposed to UV light of frequency 230 to 380 nm for 2 to 6 min.

The solvent evaporation was performed by stirring the emulsion at around 50 to 200 rpm for 24 to 72 hr.

The hardened micro or nanoparticles may be collected and washed with ultrapure water to remove excess of PVA, sodium sulfate, unreacted photo initiator, unencapsulated therapeutic agent or other excess excipients.

Preferably, the micro or nanoparticles can further be coated with mucoadhesive polymers like chitosan, sodium alginate, sodium hyaluronate, sodium carboxymethylcellulose or thiolated polymers like chitosan-cysteine, chitosan-thiobutylamidine, poly(acrylic acid)-cysteine, poly(acrylic acid)-cysteamine, carboxymethylcellulose-cysteine and alginate-cysteine to improve the retention time in the ocular tissue.

The present invention provides a method for making biodegradable photocrosslinked polymeric micro and nanoparticles that can be either applied topically to the eye surface (to treat front of the eye diseases) or administered periocularly (outside the eye) or intraocularly (inside the eye) to treat a range of eye conditions. Particularly, the particles are designed to sustain drug release ranging from 24 hrs to 3 months following a single administration. These particles are selectively crosslinked using UV light, and the degree of crosslinking of these particles and formulation composition allows control of the rate and extent of drug release over time. Furthermore, the particles can be fabricated using a variety of methods including (1) cryomilling of polymeric films to produce particles of selected sizes. This method of particles fabrication ensures stability of encapsulated therapeutic molecules, importantly for protein/peptide or gene molecules, and allows high drug encapsulation and (2) emulsification solvent evaporation method for preparation of micro and nanoparticles.

The particles are fabricated with well-known biocompatabile and biodegradable polymers, such as, PLGA and PEGDA which are crosslinked in presence of a biocompatible photoinitiator and desired therapeutic agent.

These particles can be administered in the eye by various routes such as topical, intracameral, intrascleral, transscleral, intravitreal, subretinal, and intracorneal to treat a range of eye conditions, for example, glaucoma, AMD, DR, inflammations (blepheritis), and post-surgical infections.

The present invention provides ocular compositions that can be administered to the eye in various forms to achieve controlled release of a therapeutic agent (or drug). The invention allows the flexibility to administer a range of small and large drug molecules including proteins, peptides and gene therapeutics, and maintain their activity for a controlled period of time. The invention also provides methods of treating a number of eye diseases comprising administering the ocular compositions of the invention to a subject in need thereof.

According to a first aspect, there is provided an ocular composition comprising:
  i) 99 to 60% (w/w) of a photopolymerizable composition selected from the group of fragments or monomers consisting of polyalkylene glycol diacrylate and polyalkylene glycol dimethacrylate, wherein the photopolymerizable composition has a molecular weight in the range of 200 to 20,000 Daltons;
  ii) a biodegradable polymer selected from the group consisting of aliphatic polyester-based polyurethanes, polylactides, polycaprolactones, polyorthoesters and mixtures, copolymers, and block copolymers thereof;
  iii) a photoinitiator; and
  iv) a therapeutic agent.

Optionally, the composition is used to form an ocular implant or the composition is used to coat an ocular implant.

Optionally, the implant is an in situ formed ocular implant, wherein, further optionally, the photopolymerizable composition has a molecular weight in the range of 200 to 1,000 Daltons.

Alternatively, the implant is a pre-formed ocular implant.

Optionally, the biodegradable polymer is selected from the group of collagen, chitosan, poly(propylene fumarate), lactide/glycolide copolymer (PLGA), polylactic acid (PLA), polyglycolic acid (PGA), polycaprolactone (PCL), lactide/caprolactone copolymer (PLC), poly (L-lactide) (PLLA), and mixtures, copolymers, and block copolymers thereof.

Further optionally, the biodegradable polymer is selected from the group lactide/glycolide co-polymer (PLGA), polylactic acid (PLA), polyglycolic acid (PGA), polycaprolactone (PCL), lactide/caprolactone copolymer (PLC), poly (L-lactide) (PLLA) and mixtures, copolymers, and block copolymers thereof. Still further optionally, the biodegradable polymer is PLGA.

Alternatively, the biodegradable polymer is selected from the group PCL, PLC, PLLA, and mixtures, copolymers, and block copolymers thereof.

Optionally, the photopolymerizable composition is a polyalkylene glycol diacrylate fragment or monomer incorporating diacrylate end units selected from the group comprising polyether fragments or monomers, polyester fragments or monomers, polycarbonate fragments or monomers and mixtures, copolymers, and block copolymers thereof.

Alternatively, the photopolymerizable composition is selected from the group consisting of polyethylene glycol diacrylate, diethylene glycol diacrylate, polyethylene glycol dimethacrylate, diethylene glycol dimethacrylate, polypropylene glycol diacrylate, dipropylene glycol diacrylate, dipropylene glycol dimethacrylate, and polypropylene glycol dimethacrylate.

Optionally, the photopolymerizable composition is polyethylene glycol diacrylate or polyethylene glycol dimethacrylate. Further optionally, the photopolymerizable composition is polyethylene glycol diacrylate or is PLGA.

Optionally, the molar ratio of lactic acid to glycolic acid in the PLGA is 90% lactic acid to 10% glycolic acid, 85% lactic acid to 15% glycolic acid, 75% lactic acid to 25% glycolic acid, 65% lactic acid to 35% glycolic acid, 50% lactic acid to 50% glycolic acid, 35% lactic acid to 65% glycolic acid, 25% lactic acid to 75% glycolic acid, 15% lactic acid to 85% glycolic acid, and 10% lactic acid to 90% glycolic acid.

An optional ocular composition comprises:
i) 79.5 to 59.5% (w/w) polyethylene glycol diacrylate or polyethylenene glycol dimethacrylate; and
ii) 1 to 40% (w/w) PLGA, wherein the molar ratio of lactic acid to glycolic acid in the PLGA is 90% lactic acid to 10% glycolic acid, 85% lactic acid to 15% glycolic acid, 75% lactic acid to 25% glycolic acid, or 50% lactic acid to 50% glycolic acid.

Further optionally, the ocular composition comprises:
i) 69.5% (w/w) polyethylene glycol diacrylate or polyethylene glycol dimethacrylate; and
ii) 30% (w/w) PLGA wherein the molar ratio of lactic acid to glycolic acid in the PLGA is 90% lactic acid to 10% glycolic acid, 85% lactic acid to 15% glycolic acid, 75% lactic acid to 25% glycolic acid, or 50% lactic acid to 50% glycolic acid.

An optional ocular composition of the invention comprises:
i) 95.5 to 84.5% (w/w) polyalkylene glycol diacrylate or polyalkylene glycol dimethacrylate; and
ii) 4 to 15% (w/w) PCL.

Another optional ocular composition of the invention comprises:
i) 79.5 to 94.5% (w/w) polyalkylene glycol diacrylate or polyalkylene glycol dimethacrylate; and
ii) 20 to 5% (w/w) PLLA.

Another optional ocular composition of the invention comprises:
i) 95.5 to 84.5% (w/w) polyalkylene glycol diacrylate or polyalkylene glycol dimethacrylate; and
ii) 4 to 15% (w/w) PLC in which lactic acid to caprolactone is in the range of 90% lactic acid to 10% caprolactone, 80% lactic acid to 20% caprolactone, 70% lactic acid to 30% caprolactone, 60% lactic acid to 40% caprolactone, or 50% lactic acid to 50% caprolactone.

The ocular composition of the invention optionally further comprises a solvent selected from dimethyl sulfoxide, decylmethyl sulfoxide, 2-pyrrolidone, 1-methyl-2-pyrrolidone, N-vinyl-pyrrolidine, N-Methyl-2-pyrrolidone, N-ethyl-pyrrolidone, glycerol formal, glycerol, polyethylene glycol, propylene glycol, benzyl alcohol, benzyl benzoate, ethyl benzoate, triacetin, triethyl citrate, dimethylformamide, dimethylacetamide and tetrahydrofuran. The solvent may be selected from dimethyl sulfoxide, decylmethyl sulfoxide, 2-pyrrolidone, 1-methyl-2-pyrrolidne, N-Methyl-2-pyrrolidone, and glycerol formal.

The ocular composition of the invention optionally further comprises a pore-forming agent. Optionally, the pore-forming agent is selected from polyethylene glycol, maltose, glucose, agarose, mannitol, gelatin, sodium chloride, magnesium carbonate, magnesium hydroxide, potassium chloride, sodium bicarbonate, potassium bicarbonate, and sucrose.

The photopolymerizable composition may be polymerized by irradiating the composition with light at a wavelength of between 230 to 550 nm, between 300 to 525 nm, or between 350 to 490 nm for between 1 second and 60 minutes.

Optionally, the biodegradable polymer is essentially contained within a matrix of the photopolymerizable composition.

The photoinitiator may be selected from a hydroxyketone photoinitiator, an amino ketone photoinitiator, a hydroxy ketone/benzophenone photoinitiator, a benzyldimethyl ketal photoinitiator, a phenylglyoxylate photoinitiator, an acyl phosphine oxide photoinitiator, an acyl phosphine oxide/alpha hydroxy ketone photoinitiator, a benzophenone photoinitiator, a ribityl isoalloxazine photoinitiator, or a phenylglyoxylate photoinitiator or any combination thereof. Optionally, the photoinitiator is 1-[4-(2-hydroxyethoxy)-phenyl]-2-hydroxy-2-methyl-1-propanone, 2,2-dimethoxy-2-phenylacetophenone (DMPA) or riboflavin.

The ocular composition of the invention may further comprise a co-initiator. Optionally, the photoinitiator is riboflavin and the co-initiator is L-arginine.

The ocular composition of the invention may be a nanoparticle or a microparticle ocular implant. Optionally, the nanoparticle ocular implant is less than about 1,000 nm. Optionally, the microparticle ocular implant is less than about 1,000 μm.

The method of making the nanoparticle or microparticle ocular implant, comprises the steps of:
i) mixing the therapeutic agent, the photopolymerizable composition, the biodegradable polymer and the photoinitiator, in any order of addition, to form mixture i);
ii) adding the mixture i) to an aqueous medium to form mixture ii);
iii) sonicating the mixture ii); and
irradiating the mixture ii) with light at a wavelength of between 230 to 550 nm, between 300 to 525 nm, or between 350 to 490 nm for between 1 second and 60 minutes to form the nanoparticles or microparticles.

DETAILED DESCRIPTION

Photopolymerizable Compositions

Figure 1:
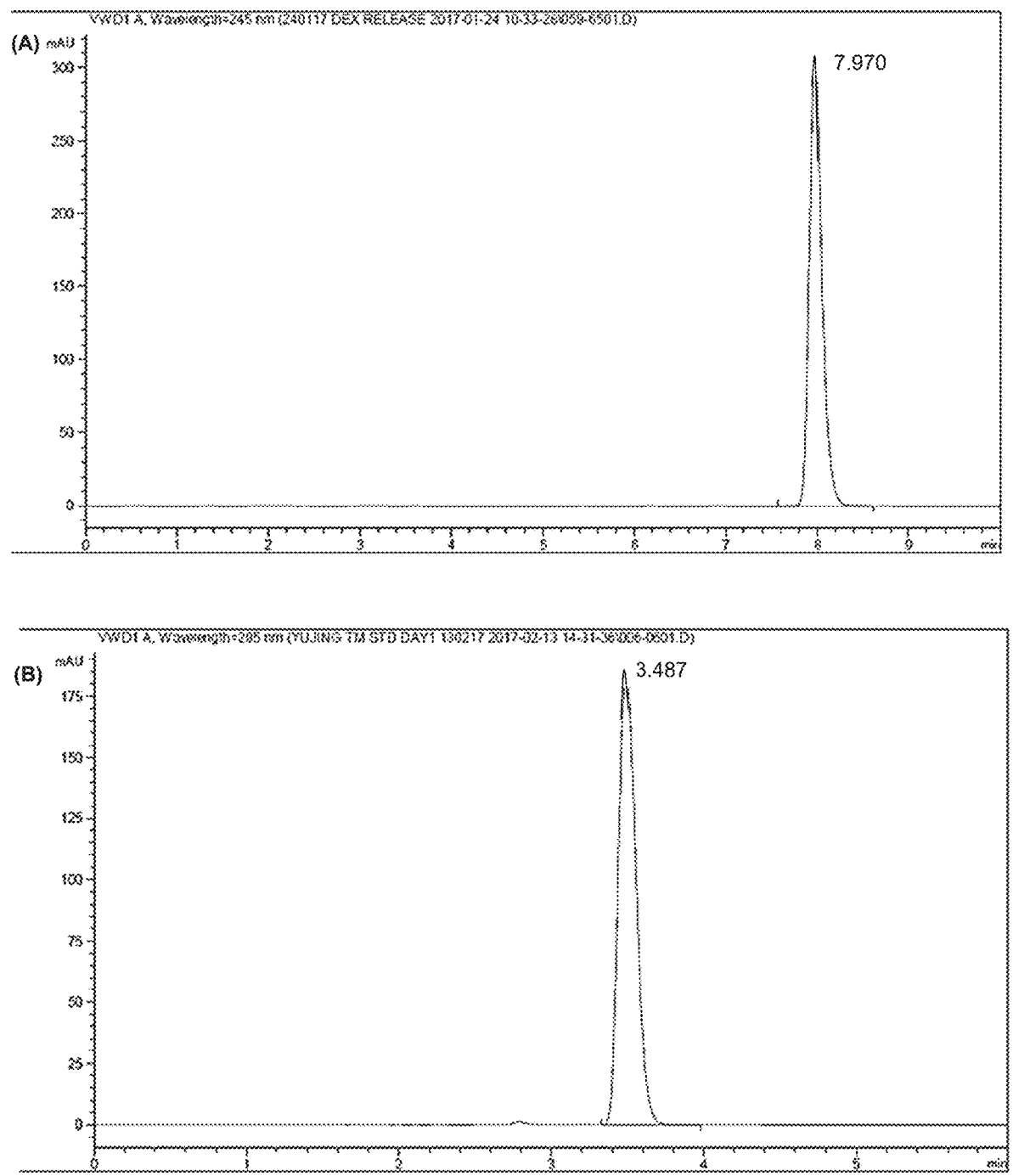
FIG. 1 shows chromatograms of A) Dexamethasone and B) Timolol maleate.

The photopolymerizable polymers of the present invention can be used in any of the compositions and implants of the invention in combination with any of the other biodegradable polymers, therapeutic agents, photoinitiators, solvents, co-solvents, pore forming agents, and co-initiators described herein or known in the common general knowledge.

In one embodiment, the photopolymerizable compositions of the invention can be biodegradable. As used herein, "biodegradable" is the chemical degradation by biological means. In some embodiments, the biodegradation is about 100%, about 98%, about 90%, about 85%, about 80%, about 60%, about 50%, or about 45% degradation of one or more of the compositions, monomers, oligomers, fragments, polymers, photoinitiators, solvents, co-solvents, or co-initiators. In some embodiments the biodegradation takes place over about 1 minute, about 10 minutes, about 20 minutes, about 2 hours, about 6 hours, about 12 hours, about 24 hours, about 2 days, about 5 days, about 1 week, about 1 month, about 2 months, about 5 months, about 6 months, about 8 months or about 12 months. In some embodiments the biodegradation takes place between about 1 month and about 12 months, between about 6 months and about 12 months, or between about 8 months and about 12 months.

As used herein, the term "photopolymerizable composition" is a composition which can form a crosslinked polymer network upon exposure to light, in particular UV light. As used herein, photopolymerizable compositions include photopolymerizable monomers and oligomers (such as, dimers, trimers, and tetramers). The terms "oligomers" and "fragments" can be used interchangeably to mean between two and twenty monomers, optionally between two and ten monomers, further optionally between two and five monomers or between two and four monomers. A "photopolymerizable monomer" is a single unit of a photopolymerizable polymer that can bind chemically to other monomers to form a polymer.

Photopolymerizable compositions of the present invention can be crosslinked with UV radiation to form photopolymerized polymers of the present invention.

In one embodiment the photopolymerizable compositions of the present invention are fragments or monomers consisting of polyalkylene glycol diacrylate, polyalkylene glycol dimethacrylate and mixtures, copolymers, and block copolymers thereof.

In one embodiment, the photopolymerizable compositions are polyalkylene glycol diacrylate fragments or monomers incorporating diacrylate end units selected from the group comprising polyether fragments or monomers, polyester fragments or monomers, polycarbonate fragments or monomers or mixtures, copolymers, or block copolymers thereof. In one embodiment, the photopolymerizable composition is a monomer incorporating diacrylate end units, such as 4-arm or 8-arm PEG acrylate.

In another embodiment, the photopolymerizable composition is polyethylene glycol diacrylate, diethylene glycol diacrylate, polyethylene glycol dimethacrylate, diethylene glycol dimethacrylate, polypropylene glycol diacrylate, dipropylene glycol diacrylate, dipropylene glycol dimethacrylate, and polypropylene glycol dimethacrylate or mixtures, copolymers, or block copolymers thereof.

In another embodiment, the photopolymerizable composition is polyethylene glycol diacrylate or polyethylene glycol dimethacrylate.

In yet another embodiment, the photopolymerizable composition is polyethylene glycol diacrylate.

The molecular weight of the photopolymerizable compositions of the present invention is typically between about 100 and about 300,000 Da, between about 200 to about 100,000 Da, between about 200 to 50,000 Da, between about 200 to about 20,000 Da, between about 200 to about 10,000 Da, between about 200 and about 8,000 Da, between about 200 and about 5,000 Da, or between about 200 and about 1,000 Da.

It has been found, for the compositions and implants of the present invention, that an increase in molecular weight of the photopolymerizable compositions results in an increase in drug release rate. Without wishing to be bound by theory, it is believed that photopolymerizable compositions with lower molecular weights have higher crosslinking density and therefore slower drug release rates.

The photopolymerizable compositions of the present invention typically have viscosities between about 0.1 to about 7 dL/g, between about 0.2 to about 5 dL/g, or between about 0.5 to 2 dL/g.

In another embodiment, the photopolymerizable compositions of the present invention are polymerized by irradiating the composition with light at a wavelength of between about 230 to about 550 nm, between about 300 to about 525 nm, or between about 350 to about 490 nm for between about 1 second and about 60 minutes, between about 30 seconds and about 30 minutes, between about 2.5 minutes and about 20 minutes, between about 5 minutes and about 10 minutes. In one embodiment, the crosslinking is for about 30 seconds, about 1, about 2.5, about 5, about 10, about 20 or about 30 minutes.

Biodegradable Polymers

The biodegradable polymers of the present invention can be used in any of the compositions and implants of the invention in combination with any of the other photopolymerizable compositions, therapeutic agents, photoinitiators, solvents, co-solvents, pore forming agents, and co-initiators described herein or known in the common general knowledge.

The biodegradable polymers of the present invention are biodegradable but not photopolymerizable.

In one embodiment of the present invention, the biodegradable polymers are aliphatic polyester-based polyurethanes, polylactides, polycaprolactones, polyorthoesters or mixtures, copolymers, or block copolymers thereof. In another embodiment of the present invention the biodegradable polymer, is chitosan, poly(propylene fumarate), lactide/glycolide copolymer (PLGA), polylactic acid (PLA), polyglycolic acid (PGA), polycaprolactone (PCL), lactide/caprolactone copolymer (PLC), poly (L-lactide) (PLLA), natural biodegradable polymers, such as, collagen and the like, or mixtures, copolymers, or block copolymers thereof. In another embodiment, the biodegradable polymer is selected from the group lactide/glycolide co-polymer (PLGA), polylactic acid (PLA), polyglycolic acid (PGA), polycaprolactone (PCL), lactide/caprolactone copolymer (PLC), poly (L-lactide) (PLLA) or mixtures, copolymers, or block copolymers thereof.

In a particular embodiment, the biodegradable polymer is PLGA. In one embodiment, the molar ratio of lactic acid to glycolic acid in the PLGA is 90% lactic acid to 10% glycolic acid, 85% lactic acid to 15% glycolic acid, 75% lactic acid to 25% glycolic acid, 65% lactic acid to 35% glycolic acid, 50% lactic acid to 50% glycolic acid, 35% lactic acid to 65% glycolic acid, 25% lactic acid to 75% glycolic acid, 15% lactic acid to 85% glycolic acid, and 10% lactic acid to 90% glycolic acid.

In another particular embodiment, the biodegradable polymer is PCL, PLC, PLLA, or mixtures, copolymers, or block copolymers thereof.

Compositions and Implants

In one embodiment, the compositions of the invention comprise combinations of photopolymerizable compositions, and biodegradable polymers, as described above, in combination with a photoinitiator and a therapeutic agent, which can be delivered to the eye to achieve controlled drug delivery to treat a range of eye diseases. The compositions of the invention include:

i) compositions which can be injected into the eye followed by application of short-term UV light to induce in situ photocrosslinking, resulting in implant formation, termed as in situ photocrosslinked implants (ISPcI); and ii) compositions which can be photocrosslinked prior to application in the eye to form an implant of desired shape and size (e.g., film, rod or nano/microparticles) that can be administered intraocularly to provide desired period of drug delivery, termed as performed photocrosslinked implants (PPcI).

Alternatively, the compositions of the invention can be used to coat ocular devices, including both in situ and pre-formed ocular devices.

The implants of the present invention can be any desired shape and size, such as but not limited to, for example rectangular, square, cylindrical, circular, oval, films, dumbbell, rods, beads, etc., as, for example, macro, micro or nanoparticles.

The ocular implant is a nanoparticle or a microparticle.

In one embodiment, the nanoparticle ocular implant is less than about 1,000 nm, less than about 900 nm, less than about 750 nm, less than about 500 nm, or less than about 100 nm.

In one embodiment, the microparticle ocular implant is less than about 1,000 µm, less than about 900 µm, less than about 750 µm, less than about 500 µm, or less than about 25 µm.

In Situ Photocrosslinked Implants (ISPcI)

In situ photocrosslinked implants (ISPcI), of the present invention are those that form and take up their final localised structure once they are inserted into the body. The ability of these implants to fill irregular defects is an advantage of ISPcIs. The ISPcIs of the present invention also have additional advantages, which include, site-specific action due to relatively easy and less invasive application, localized delivery to specific tissues, prolonged delivery times, reduction in side effects linked with systemic delivery and also superior patient comfort and compliance. Additional advantages of the ISPcIs of the present invention include, not requiring extreme pH conditions or elevated temperatures during processing, which could cause issue when working with temperature or pH labile drugs (e.g., proteins, peptides or genetic material). Furthermore, rapid crosslinking at physiological temperatures can swiftly entrap drug molecules and can result in an ISPcI that possesses the exact required dimensions for controlled drug release. Photocrosslinking is also beneficial in comparison to spontaneous crosslinking (e.g., enzymatic, self-assembled, Michael addition) as the initiation of the process is only triggered when exposed to a light source, therefore premature gelation is not an issue resulting in excellent control of material formation. Furthermore, short-term application of UV light will not cause any safety issues as it is considered safe for ocular applications, as UV light is clinically used for corneal crosslinking. Importantly, administration by this method allows the injection of a relatively low viscosity material into the body, which then solidifies to form a semi-solid depot that controls the drug delivery to provide short or long-term therapeutic action.

In one embodiment, the ISPcIs of the present invention are formed by injection of a composition of the invention into a subject in need thereof and subsequent crosslinking using external source of UV light that results in formation of a solid implant which controls drug release for desired period of time.

For ISPcIs of the invention the molecular weight of the photopolymerizable composition is typically between about 100 and about 6,000 Da, between about 200 and about 3,000 Da, or between about 200 and 1,000 Da.

Preformed Photocrosslinked Implants (PPcI)

In one embodiment, the present invention is a preformed photocrosslinked implant (PPcI). These PPcIs can be inserted in the eye (e.g., in the fornix, subconjunctively, intracameral, intrastromal/intracorneal, transsclerally/periocular, intrasclerally or intravitreally) to treat the front of the eye or back of the eye diseases. These implants can be fabricated in a variety of shapes (e.g., rods, films, cylindrical or circular) and sizes, including in the form of micro or nanoparticles. The implants can also be fabricated as electrospun fibres or electrospun mats using electrospinning technology.

The PPcIs of the present invention have the advantage of high crosslink density and/or a tight polymer network structure which can be configured to control drug release and/or eliminate any burst release.

The PPcIs of the present invention can be fabricated to have a single and/or multiple layers, which will enable loading of more than one drug or the same drug with different release profiles or rates.

Furthermore, the rate of degradation of the implants can be slower for PPcIs when compared to ISPcIs of the invention and can be altered to treat specific diseases or disorders.

For the PPcIs of the invention the molecular weight of the photopolymerizable polymers is typically between about 100 and about 300,000 Da, between about 200 to 100,000 Da, between about 200 to 50,000 Da, between about 200 to 20,000 Da, or between about 200 to about 10,000 Da.

In one embodiment, the biodegradable polymer is essentially contained within a matrix of the photopolymerizable composition. In one embodiment, the biodegradable polymer is essentially contained within a matrix of the photopolymerizable composition that forms a gel upon mixing. In one embodiment the photopolymerizable polymer is crosslinked in presence of a photoinitiator and the biodegradable polymer and therapeutic agent(s). In one embodiment, the biodegradable polymer is essentially trapped within the crosslinked photopolymerizable polymer matrix, and the therapeutic agent(s) are either dispersed or dissolved between the two phases (i.e., photopolymerizable and/or biodegradable polymer). In one embodiment, the biodegradable polymer is hydrophobic in nature and the photopolymerizable polymer is hydrophilic in nature. In one embodiment, the degree of crosslinking of the composite implant will govern the rate and extent of release of the therapeutic agent(s).

In yet another embodiment, the implants are coated with single or multiple layers with polymers such as PLGA, PCL, PLA, and PLC to further control the release of therapeutic molecule. The coating can be achieved by a number of methods, preferably by dip coating in organic solvents containing polymers such as PLGA, PCL, PLA, and PLC.

In another embodiment, the present invention is an ocular composition wherein i) and ii) are:
i) 79.5% (w/w) polyethylene glycol diacrylate or polyethylene glycol dimethacrylate; and
ii) 30% (w/w) PLGA wherein the molar ratio of lactic acid to glycolic acid in the PLGA is 90% lactic acid to 10% glycolic acid, 85% lactic acid to 15% glycolic acid, 75% lactic acid to 25% glycolic acid, or 50% lactic acid to 50% glycolic acid.

In another embodiment, the present invention is an ocular composition wherein i) and ii) are:
i) 95.5 to 84.5% (w/w) polyalkylene glycol diacrylate or polyalkylene glycol dimethacrylate; and
ii) 4 to 15% (w/w) PCL.

In another embodiment, the present invention is an ocular composition wherein i) and ii) are:
i) 69.5 to 94.5% (w/w) polyalkylene glycol diacrylate or polyalkylene glycol dimethacrylate; and
ii) 20 to 5% (w/w) PLLA.

In yet another embodiment, the present invention is an ocular composition wherein i) and ii) are:
i) 95.5 to 84.5% (w/w) polyalkylene glycol diacrylate or polyalkylene glycol dimethacrylate; and
ii) 4 to 15% (w/w) PLC in which lactic acid to caprolactone is in the range of 90% lactic acid to 10% caprolactone, 80% lactic acid to 20% caprolactone, 70% lactic acid to 30% caprolactone, 60% lactic acid to 40% caprolactone, or 50% lactic acid to 50% caprolactone.

In one embodiment, the present invention is an ocular composition wherein i) is 95.5 to 84.5% (w/w) polyalkylene glycol diacrylate or polyalkylene glycol dimethacrylate; and wherein ii) is 4 to 15% (w/w) PCL.

In one embodiment, the % of the biodegradable polymer is 30% w/w, 5% w/w. 2.5% w/w, between 4-10% w/w, or between 5-18% w/w.

In one embodiment, i) and ii) of the compositions of the present invention are PEGDA and PLGA.

PLGA

PLGA is prepared by polymerisation of lactic acid and glycolic acid monomers. The glass transition temperatures ($T_g$) of PLGA copolymers are above physiological temperatures of 37° C., which imparts a moderately rigid chain configuration and therefore the mechanical strength at ambient temperatures. The use of PLGA in different lactide (LA) to glycolide (GA) ratio and molecular weight allows different drug release profiles. An increase in GA content will result in an increased water uptake of PLGA and therefore more rapid degradation. The degradation of PLGA with LA/GA 50/50 is typically between about 1 and about 3 months.

PEGDA

PEGDA is a synthetic polymer, available in different $M_w$. PEGDA is extremely amenable to mechanical, structural and chemical alteration and so resulting in hydrogels with variable properties in terms of drug delivery and other biomedical applications. PEGDA is formed through the functionalization of the end of each PEG molecule with an acrylate group. PEGDA is also non-toxic, eliciting only a minimal immunogenic response. PEGDA has double-bond containing acrylate end groups which show rapid polymerisation when exposed to light in the presence of an appropriate initiator to produce a hydrogel network.

In one embodiment, the present invention is a PLGA/PEGDA PPcI.

In one embodiment, the present invention is a PLGA/PEGDA ISPcI.

Copolymers

All of the copolymers and block copolymers described herein can be used in any of the compositions and implants of the invention in combination with any of the other photopolymerizable compositions, biodegradable polymers, therapeutic agents, photoinitiators, solvents, co-solvents, pore forming agents, and co-initiators described herein.

As used herein "copolymer" is a mixture of two or more different types of monomer units. As used herein "block copolymer" is a mixture of two or more homopolymer subunits.

In one embodiment, block or copolymers with PGA, PCL, PLA, PLGA that would include any other polymeric component of the polymer e.g., PEG and PEO, for example, PLGA-PEO, PCL-PEO and PEG-PLGA, PEG-PCL block copolymers, which include, for example, PEO-PLGA-PEO, PLGA-PEG, PLGA-PEO, and PLGA-PEO-PLGA.

Solvents

All of the solvents described herein can be used in the preparation of any of the compositions and implants of the invention in combination with any of the other photopolymerizable compositions, biodegradable polymers, therapeutic agents, photoinitiators, pore forming agents, and co-initiators described herein.

In one embodiment, the co-solvents used in the present invention can be selected from dichloromethane, tetrahydrofuran, ethyl acetate, acetone, dimethylformamide, acetonitrile, acetic acid, methanol, ethanol, isopropanol, glycofurol or butanol.

In one embodiment, the solvents used in the present invention are dimethyl sulfoxide, decylmethyl sulfoxide, 2-pyrrolidone, N-vinyl-2-pyrrolidone, 1-methyl-2-pyrrolidone, N-Methyl-2-pyrrolidone, N-ethyl-pyrrolidone, glycerol formal, glycerol, polyethylene glycol, propylene glycol, benzyl alcohol, benzyl benzoate, ethyl benzoate, triacetin, triethyl citrate, dimethylformamide, dimethylacetamide or tetrahydrofuran.

In another embodiment, the solvent is dimethyl sulfoxide, decylmethyl sulfoxide, 2-pyrrolidone, 1-methyl-2-pyrrolidone, N-Methyl-2-pyrrolidone, or glycerol formal.

In one embodiment, a solvent is used when the biodegradable polymer is PCL, PLC and/or PLLA. In one embodiment the solvent is N-Methyl-2-pyrrolidone and N-Vinyl-2-pyrrolidine when the biodegradable polymer is PCL, PLC and/or PLLA. In another embodiment, a solvent is used when the photomolymerizable composition is PEGDA.

Pore Forming Agents

In one embodiment, a suitable pore forming agent may be selected in view of the specific therapeutic agent and composition of the implant, and the desired elution profile or release rate. The pore forming agent may be a naturally occurring agent or polymer or a synthetic agent or polymer.

In another embodiment, implant porosity can be adjusted by preparing implants in the presence of dispersed water-soluble porosigens, which can be removed later by washing with water to leave an interconnected meshwork (i.e., porous hydrogels). The pore size of hydrogels prepared by the porosigen technique depends on the size of the porosigens.

All of the pore forming agents described herein can be used in any of the implants and compositions of the invention in combination with any of the other photopolymerizable compositions, biodegradable polymers, therapeutic agents, photoinitiators, solvents, co-solvents, and co-initiators described herein.

In one embodiment, the compositions of the invention further comprise a pore-forming agent.

In one embodiment, the pore-forming agent is polyethylene glycol, lactose, maltose, glucose, mannitol, gelatin, sodium chloride, magnesium carbonate, magnesium hydroxide, potassium chloride, sodium bicarbonate, ammonium bicarbonate, potassium bicarbonate, chitosan, polyvinylpyrrolidone, polyvinyl alcohol, agarose or sucrose.

Photoinitiators

In one embodiment, the compositions of the invention further comprise a photoinitiator.

The photoinitiators described herein can be used in any of the compositions and implants of the present invention in combination with any of the other photopolymerizable compositions, biodegradable polymers, therapeutic agents, photoinitiators, solvents, co-solvents, and co-initiators described herein.

In certain embodiments, the photoinitiator is designed to work using light from about 200 to about 550 nm. In some embodiments, a photoinitiator is designed to work using UV light from about 200 to about 400 nm.

In certain embodiments, the light source may allow variation of the wavelength of light and/or the intensity of the light. Light sources useful in the present invention include, but are not limited to, lamps, fiber optics devices, etc.

In one embodiment, the photoinitiator is a ketone (e.g., RCOR'). In one embodiment, the compound is an azo compound (e.g., compounds with a —N=N— group). In one embodiment, the photoinitiator is an acylphosphineoxide. In one embodiment, the photoinitiator is a sulfur-containing compound. In one embodiment, the initiator is a quinone. In certain embodiments, a combination of photoinitiators is used.

In one embodiment, the photoinitiator is a hydroxyketone photoinitiator, an amino ketone photoinitiator, a hydroxy ketone/benzophenone photoinitiator, a benzyldimethyl ketal photoinitiator, a phenylglyoxylate photoinitiator, an acyl phosphine oxide photoinitiator, an acyl phosphine oxide/ alpha hydroxy ketone photoinitiator, a benzophenone photoinitiator, a ribityl isoalloxazine photoinitiator, or a phenylglyoxylate photoinitiator or any combination thereof.

In one embodiment the photoinitiator is 1-[4-(2-hydroxy-ethoxy)-phenyl]-2-hydroxy-2-methyl-1-propanone, 2,2-dimethoxy-2-phenylacetophenone (DMPA) or riboflavin.

In one embodiment, the compositions of the present invention further comprise a co-initiator. In one embodiment, the co-initiator is eosin Y, triethanolamine, camphorquinone, 1-vinyl-2 pyrrolidinone (NVP), eosin, dimethylaminobenzoate (DMAB), Irgacure® 907 (Ciba Geigy), Irgacure® 651 (Ciba Geigy), Darocur 2959 (Ciba Geigy), or ethyl-4-N,N-dimethylaminobenzoate (4EDMAB).

In one embodiment, the photoinitiator is riboflavin and the co-initiator is L-arginine.

Process

The compositions and implants of the present invention can be made by any methods know in the art as well as the methods described herein. The methods described herein are applicable to all compositions and implants of the invention.

In one embodiment, polymer $M_w$, type and copolymer ratio, drug type and loading, implant size, time and extent of UV crosslinking and/or amount and type/concentration of photoinitiator and/or pore forming agent (porogen) and/or solvent/co-solvent can be altered to control the rate and extent of drug release. The alteration of these factors provides compositions of the invention that can be easily tailored to produce desired period of drug release to address specific clinical/patient needs in treating various ocular diseases.

In the compositions of the present invention, varying the UV crosslinking time can control the rate of and duration of drug release. In some embodiments, an increase in UV crosslinking times causes a decrease in drug release. Additionally, varying the concentration of the photoinitiator can control the rate and duration of drug release. Furthermore, varying both the UV crosslinking time and the concentration of photoinitiator can control the rate and duration of drug release. In one embodiment, decreasing the concentration of the biodegradable polymer (such as PLGA) increases the drug release rate. In one embodiment, adding a pore-forming agent (e.g., $MgCO_3$), increases the drug release rate. In one embodiment, higher UV crosslinking time and higher concentration of photoinitiator can sustain the drug release for longer periods of time. In one embodiment, the drug release can be sustained for a period of greater than about 1 day, about 2 days, about 1 week, about 1 month, about 2 months, about 3 months, or about 6 months.

In one embodiment, the duration of drug release in the ISPcIs of the present invention can be considerably extended, for example, providing controlled drug release fora period of greater than 200 days (>6 months). This duration can be varied by varying the degree of crosslinking.

In some embodiments, the slow degradation rate of the ISPcIs of the present invention provide protection of the sensitive molecules such as peptides and proteins. It has been shown below, that the ISPcIs of the present invention are stable and avoid protein degradation and maintain protein activity.

In some embodiments, burst release can be eliminated or controlled by varying the UV crosslinking time.

In one embodiment, the present invention is a PPcI with no burst release. In one embodiment, the present invention is a PPcI with high crosslinking density that significantly slows drug diffusion.

Methods of Use

Any of the implants and compositions described herein are suitable for use in any of the methods of the invention described herein.

In one embodiment, the present invention is a method of treating a disease or disorder of the eye in a subject in need thereof, comprising administering a composition or implant of the present invention to an ocular area of the subject.

In one embodiment, the present invention is a composition or implant of the present invention for use in treating a disease or disorder of the eye in a subject in need thereof.

As used herein, an "ocular area" is an area inside, outside or adjacent to the eye of the subject. In one embodiment, the ocular area is the sclera (intrascleral), outside the sclera (transscleral), the vitreous body, the choroid, supra choroidal space, the cornea, the stroma, intracameral, the aqueous humor, the lens, the fornix, surface of the eye (topical) or the optic nerve.

In one embodiment, the compositions and implants can be administered by injection, including, intravitreal, subconjunctival, peribulbar, subtenon or retrobulbar injections and cornea.

In some embodiments, the implants are administered via a surgical procedure. In some embodiment, the implants are secured in place, after surgical implantation, via an adhesive or sutures.

In some embodiments, it can be simply applied on the eye or inserted in the puncta The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

As used herein, the terms "treat", "treatment" and "treating" refer to therapeutic treatments includes the reduction or amelioration of the progression, severity and/or duration of a disease, disorder or condition, or the amelioration of one or more symptoms (specifically, one or more discernible symptoms) of a disease, disorder or condition, resulting from the administration of the compositions or implant of the invention. In specific embodiments, the therapeutic treatment includes the amelioration of at least one measurable physical parameter of a disease, disorder or condition. In other embodiments the therapeutic treatment includes the inhibition of the progression of a condition, either physically by, e.g., stabilization of a discernible symptom, physiologically by, e.g., stabilization of a physical parameter, or both. In other embodiments the therapeutic treatment includes the reduction or stabilization of a disease, disorder or condition.

Exemplary therapeutic agents include, but are not limited to, polypeptides, nucleic acids, such as DNA, RNA, and siRNA, growth factors, steroid agents, antibody therapies, antimicrobial agents, antibiotics, antiretroviral drugs, anti-inflammatory compounds, antitumor agents, anti-angiogenic agents, and chemotherapeutic agents.

In one embodiment, the therapeutic agent of the present invention includes, but is not limited to, ketorolac, naphazoline, lidocaine, bevacizumab, aflibercept, pegaptanib, brimonidine, dorzolamide, azithromycin, rapamycin, bepotastine besilate, diclofenac, besifloxacin, cysteamine hydrochloride, fluocinolone acetonide, difluprednate, aflibercept, tasimelteon, ocriplasmin, enoxaparin sodium, ranibizumab, latanoprost, timolol, bimatoprost, pegaptanib, ofloxacin, cephazolin, phenylephrine, dexamethasone, triamcinolone acetonide, levofloxacin, cyclophosphamide, melphalan cyclosporine, methotrexate, azathioprine ketorolac, travoprost, verteporfin, tafluprost, ketotifen fumarate, foscarnet, amphotericin B, fluconazole, voriconazole, ganciclovir, acyclovir, gatifloxacin, vitamin (vitamin A, vitamin C, and vitamin E), zinc, copper, lutein, zeaxanthin or combinations thereof.

In one embodiment, the compositions or implants of the present invention can deliver bioactive agent, a large molecular weight drug, such as, aflibercept, pegaptanib, or an antibody therapeutic, such as ranibizumab, bevacizumab, trastuzumab, rituximab, gentuzumab, ozagamicin or cetuximab. In some embodiment, the $M_w$ of the therapeutic agent is greater than about 10 kDa, about 30 kDa, about 50 kDa, about 75 kDa, about 100 kDa, about 150 kDa, about 200 kDa.

In one embodiment, the disease, or disorder is pain, inflammation, cataracts, allergies, age-related macular degeneration (AMD), diabetic retinopathy (DR), macular edema, diabetic macular edema (DME), cytomegalovirus (CMV), retinitis, retinitis pigmentosa, uveitis, dry-eye syndrome, keratitis, glaucoma, blepharitis, blephariconjunctivtis, ocular hypertension, conjunctivitis, cystinosis, vitreo-macular adhesion, corneal neovascularisation, corneal ulcers and post-surgical ocular inflammations/wound healing.

EXAMPLES

Materials

The following methods and materials were used in the Examples below.

Poly(lactic-co-glycolic acid) (PLGA) 5002A (50% lactic acid, 50% glycolic acid monomers) and PLGA 7502A (75% lactic acid, 25% glycolic acid) (referred to as PLGA50/50 and PLGA75/25 respectively throughout) was purchased from Corbion Purac Biomaterials (Gorinchem, The Netherlands). Poly(ethylene glycol) diacrylate (PEGDA) molecular weight ($M_w$) 258, 575 and 700 Da, ovalbumin (OVA), bovine serum albumin (BSA), Irgacure 2959 (1-[4-(2-hydroxyethoxy)-phenyl]-2-hydroxy-2-methyl-1-propanone), methanol (HPLC grade) and acetonitrile (ACN) (HPLC grade) were purchased from Sigma-Aldrich (Dorset, United Kingdom). Triamcinolone acetonide (TA) and dexamethasone (DEX) was purchased from Spruyt Hillen by (Ijsselstein, The Netherlands). Bevacizumab (BVZ) (Avastin®) was purchased from local pharmacy (manufactured by Roche, Switzerland; each vial consists of 100 mg BVZ in 4 mL i.e, 25 mg/ml). Fluorescein isothiocyanate-dextran (FITC-Dextran) ($M_w$ 150 kDa) was purchased from TdB Consultancy AB (Uppsala, Sweden). 27G needles and 1 ml syringes were purchased from Terumo Europe N.V. (Interleuvenlaan, Belgium). Rabbit anti-OVA-biotin conjugate (polyclonal) was purchased from Novus Biologicals (Cambridge, United Kingdom). Streptavidin-Horse radish peroxidase conjugate was purchased from BioLegend® (San Diego, United States). Superblock T20 buffer was purchased from Thermo Scientific Pierce (Rockford, United States).

Nano and Micro-Particulate Formulations for Sustained Ocular Drug Delivery

The following studies were developed and validated to illustrate the invention for two-drug molecules viz. Dexamethasone and Timolol maleate. Photo-crosslinked microparticles (PcMPs) were prepared using Dexamethasone as model drug.

The methodology and results and discussion for these PcMPs is described in detail in the following sections.

Methodology:

A) Analytical Method:

Analytical method for Dexamethasone and Timolol maleate was developed using reverse phase high-performance liquid chromatography (HPLC) method.

a) Instrumentation:

The HPLC instrument consisted of Agilent 1260 Infinity pump equipped with a sample injection port fitted with 20 µl sample loop, a UV-VIS detector and a Chromato-Integrator (Agilent Technologies, Germany).

b) Chromatographic Condition for Dexamethasone:

The mobile phase consisted of Acetonitrile: Water in the ratio 40:60. The flow rate of mobile phase was 0.8 mL/min and the eluted drug was detected at 245 nm wavelength. Chromatographic separation of the dexamethasone was achieved at ambient room temperature (24±2° C.) using Poroshell 120 EC-C18 4 µm (250× 4.60 mm) analytical column fitted with a refillable guard column. The mobile phase was filtered by passing through 0.45 µm membrane filter (Whatman International, UK) under vacuum and degassed before use.

c) Chromatographic Condition for Timolol Maleate:

The mobile phase consisted of Acetonitrile with 0.05% v/v Trifluoroacetic acid: Water with 0.05% Trifluoroacetic acid in the ratio 40:60. The flow rate of mobile phase was 0.8 mL/min and the eluted drug was detected at 295 nm wavelength. Other conditions were like Dexamethasone analytical method.

d) Analytical Method Validation:

The analytical methods were validated per the guidelines of the International Conference on Harmonization (ICH) of technical requirements for registration of pharmaceuticals for human use in terms of linearity, accuracy, precision (intra-day and inter-day) and system suitability.

B) Photo Crosslinked Microparticles (PcMPs) Preparation:

Dexamethasone loaded microparticles were prepared using a film-casting and freeze-milling technique.

Weighed amount of poly (lactic-co-glycolic acid) PLGA (50:50) polymer was dissolved in Poly (ethylene glycol) diacrylate PEGDA (Mn=700) polymer followed by addition of Dexamethasone. The mixture was stirred overnight. In another vial, weighed amount of photo-initiator Irgacure 2959 was dissolved in 0.5 mL Acetone and added to drug-polymer mixture just before starting the UV exposure. The polymer mixture with Irgacure was added to Petri dish to cast a thin film and formulation was exposed to UV light for 96 sec at 93% intensity of UV lamp (Light Hammer 6, Fusion UV systems, Inc., USA).

The formed films were grinded in a ball mill (MM400 Mixer Mill, Retsch GmbH, Germany) at −196° C. using liquid nitrogen. The polymer film was initially crushed using mortar-pestle and then introduced in sample cells along with stainless steel balls. The sample cells were then cooled by immersing in Liquid nitrogen and then loaded into the mill. The mill was run for 3 min at 25 Hz frequency followed by cooling in Liquid nitrogen and again ran for 3 min. The cycle was repeated 5 times. The microparticles were sieved and separated into 3 different sizes/size ranges as below:

TABLE 1

PcMPs formulations

| Formulation Composition of MPs | Particle Size Groups (Size, μm) | Formulation Code |
|---|---|---|
| 30% w/w PLGA, 2% w/w DEX, 67.5% w/w PEGDA 700 | <45 | F11 |
| | 45-90 | F12 |
| | 90-212 | F13 |
| 50% w/w PLGA, 2% w/w DEX, 47.5% w/w PEGDA 700 | <45 | F21 |
| | 45-90 | F22 |
| | 90-212 | F23 |
| 0% w/w PLGA, 2% w/w DEX, 97.5% w/wPEGDA 250 | <45 | F31 |
| | 45-90 | F32 |
| | 90-212 | F33 |
| 0% w/w PLGA, 2% w/w DEX, 97.5% w/w PEGDA 700 | <45 | F41 |
| | 45-90 | F42 |
| | 90-212 | F43 |

PLGA = poly (lactic-co-glycolic acid), DEX = Dexamethasone, PEGDA = Poly (ethylene glycol) diacrylate C) Characterization of PcMPs:

1. Microparticles were characterized for size distribution by laser diffractometer (Helos/BR, Sympatec GmbH, Germany). Small amount (~5 mg) of MPs were dispersed in 0.01% Tween 20 solution and introduced in sample cell.
2. Particle size and morphology was assessed using Bench Top Scanning Electron Microscope (SEM) (TM3030, Hitachi, Japan).
3. Thermal analysis was performed using DSC Q100 (TA instruments, USA). Weighed amount of polymers, drug and PcMPs were heated individually in Aluminium pans from −60° C. to 80° C. (Polymers), 0° C. to 300° C. (Dexamethasone) and −60° C. to 350° C. (PcMPs)

at heating rate of 3° C./min. Graphs of Temperature Vs Heat flow were drawn to study changes in polymer glass transition temperature (Tg) and Dexamethasone melting temperature (Tm).

D) In Vitro Release Study:

Microparticles were prepared in different combinations of polymers, keeping drug loading constant, were subjected to drug release study.

Formulations mentioned in the Table 1 were used to study effect of particle size on drug release. 40 mg of MPs were incubated in 50 mL phosphate buffer pH 7.2 at 37° C. and 40 rpm (ISF-7100 Incubated shaker, Jeio Tech, Korea). At predetermined time intervals, 1 mL of supernatant was removed and analysed for dexamethasone content by validated HPLC method. To maintain sink condition, 1 mL fresh buffer was added to release medium.

Figure 12:
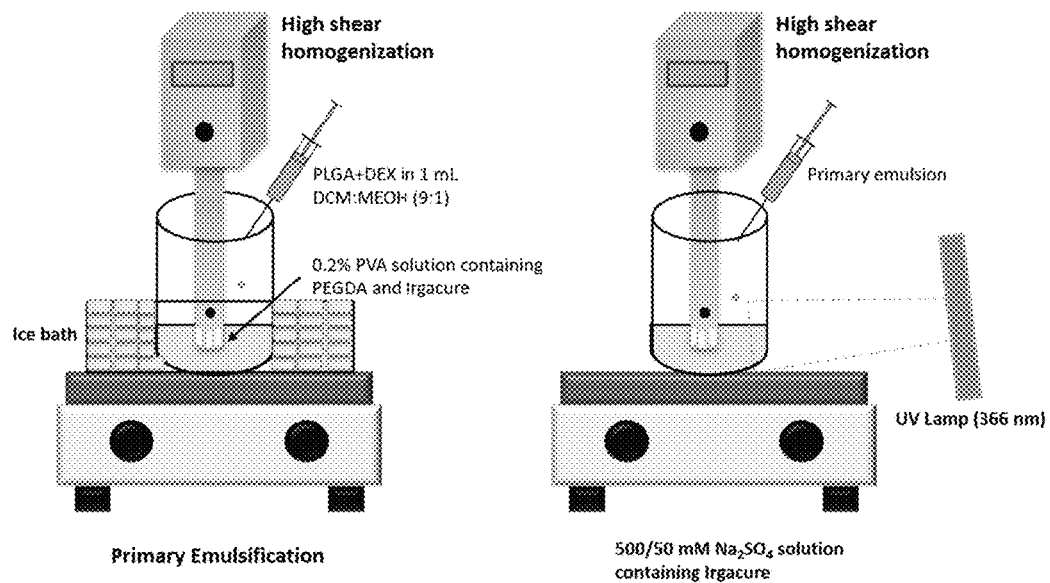
FIG. 12 depicts preparation of PcMPs using emulsification precipitation method.

E) Emulsification Evaporation-Precipitation Method for Preparation of Micro- and Nano-Particles:

A new method was developed to prepared photo crosslinked microparticles/nanoparticles (FIG. 12). Briefly, 100 mg PLGA and 10 mg dexamethasone were dissolved in 1 mL of dichloromethane:methanol (9:1) solvent mixture. This solution was then added to 5 mL 0.2% w/v polyvinyl alcohol (PVA, MW=~9000) containing 390 mg PEGDA polymer with homogenization at 10,000 rpm for 2 min. Alternatively, PEGDA polymer can also be dissolved in dexamethasone-PLGA mixture and added to 0.2% PVA solution containing 0.2% w/v Irgacure and homogenized at 10,000 rpm for 2 min. Alternatively, the emulsion can also be prepared by adding dexamethasone-PLGA (with or without PEGDA) into 0.01 to 0.5% w/v d-α-tocopheryl polyethylene glycol 1000 succinate (vitamin E TPGS or TPGS) or 0.1 to 2% w/v polysorbate 80 (Tween 80) or 0.1 to 1% w/v Poloxamer 188 when used as emulsifiers.

The emulsion formed was then added to 5 mL 500 mM sodium sulfate decahydrate solution containing 0.2% w/v Irgacure (previously dissolved in 100 μl Methanol) with homogenization at 10,000 rpm for 4 min.

The emulsion was then stirred at 300 rpm and exposed to UV light of frequency 366 nm for 5 min. The solvent evaporation was performed by stirring the emulsion at 100 rpm for 48 hr. The hardened particles were collected and washed with ultrapure water to remove excess of PVA and sodium sulfate salt.

Higher homogenization speed and higher surfactant concentration were used to further reduce the size to nanometer range.

The particles can further be coated with mucoadhesive polymers like chitosan, sodium alginate, sodium hyaluronate, sodium carboxymethylcellulose or thiolated polymers like chitosan-cysteine, chitosan-thiobutylamidine, poly (acrylic acid)-cysteine, poly(acrylic acid)-cysteamine, carboxymethylcellulose-cysteine and alginate-cysteine to improve the retention time in the ocular tissue.

F) Characterization of PcMPs Prepared by Novel Emulsification Precipitation Method:

The microparticles were characterized for size distribution by laser diffractometer (Helos/BR, Sympatec GmbH, Germany).

Particle size and morphology was assessed using Bench Top Scanning Electron Microscope (SEM) (TM3030, Hitachi, Japan).

In vitro release was performed to compare release of dexamethasone from PcMPs prepared by two different methods and with non-crosslinked PLGA microparticles.

In vitro release study was performed by incubating 500 μl of MPs suspension containing 25 mg of MPs (PLGA MPs, PLGA-PEGDA PcMPs by emulsification precipitation method and freeze milled PLGA-PEGDA PcMPs) in 50 mL phosphate buffered saline at 37° C. (horizontal shaking speed 40 rpm). At predetermined timepoints, 1 mL sample was withdrawn and replaces by 1 mL fresh buffer. Dexamethasone released was quantified by validated HPLC method.

Fourier Transform Infrared (FTIR) spectroscopy was performed to analyse the interactions between microparticle components as well as differences between cross-inked and non-crosslinked MPs.

G) Optimization of PcMPs:

The PcMPs were further optimized with respect to the drug (Dexamethasone) drug loading viz. 2%, 5% and 10% w/w basis.

In vitro dexamethasone release from these PcMPs was performed to check effect of drug loading on release pattern.

Due to instability of dexamethasone in phosphate buffer for long term release, triamcinolone acetonide (TA), another anti-inflammatory corticosteroid was selected for further optimization. To reduce the initial burst effect, photo-crosslinking time was increased. The photo-crosslinking time was kept as 5, 15, 30 and 60 min. which the time formulations were exposed to UV light at 366 nm. The prepared formulations were characterized for size and in vitro drug (TA) release.

Results and Discussion

A) Analytical Method:

The method for DEX was developed by varying different parameters like mobile phase components, mobile phase composition and flow rate. Finally, dexamethasone was eluted isocratically at a flow rate of 0.8 ml/min using mobile phase concentration of acetonitrile and water (40:60 v/v). Calibration curve was constructed in the concentration range of 1-50 μg/ml, showing very good linearity with correlation coefficient of 1.0000.

Chromatograms for Dexamethasone and Timolol maleate are shown in FIG. 1.

Table 2 summarizes the validation parameters of the developed analytical method while Table 3 summarizes system suitability parameters, which agree with the ICH guidelines for validation of analytical procedures.

TABLE 2

Validation parameters for Dexamethasone

| Parameter | Values ± SD |
|---|---|
| Range | 1.00-50.00 μg/ml |
| Linearity ($R^2$) | 1.0000 ± 0.0001 |
| Slope | 60.50 ± 1.45 |
| Intercept | −3.16 ± 4.35 |
| LOD | 0.24 μg/ml |

TABLE 2-continued

Validation parameters for Dexamethasone

| Parameter | Values ± SD |
|---|---|
| LOQ | 0.72 μg/ml |
| % RSD | 1.43 |

TABLE 3

System suitability parameters for Dexamethasone

| Parameter | Values |
|---|---|
| Theoretical plates | 16,770 |
| Tailing factor (USP) | 1.29 |
| Peak Asymmetry factor | 1.24 |
| Capacity factor | 2.945 |

Good linearity of 0.9995 was achieved for Timolol maleate in the concentration range of 0.5-100 μg/ml.

Validation and System suitability parameters for Timolol maleate are summarized in Table 4 and 5 respectively.

TABLE 4

Validation parameters for Timolol maleate

| Parameter | Values ± SD |
|---|---|
| Range | 5-100.00 μg/ml |
| Linearity ($R^2$) | 0.9995 ± 0.0004 |
| Slope | 30.26 ± 0.63 |
| Intercept | −5.17 ± 6.77 |
| LOD | 0.74 μg/ml |
| LOQ | 2.24 μg/ml |
| % RSD | 0.0904 |

TABLE 5

System suitability parameters for Timolol maleate

| Parameter | Values |
|---|---|
| Theoretical plates | 5,068 |
| Tailing factor (USP) | 1.25 |
| Peak Asymmetry factor | 1.22 |
| Capacity factor | 3.4567 |

Figure 2:
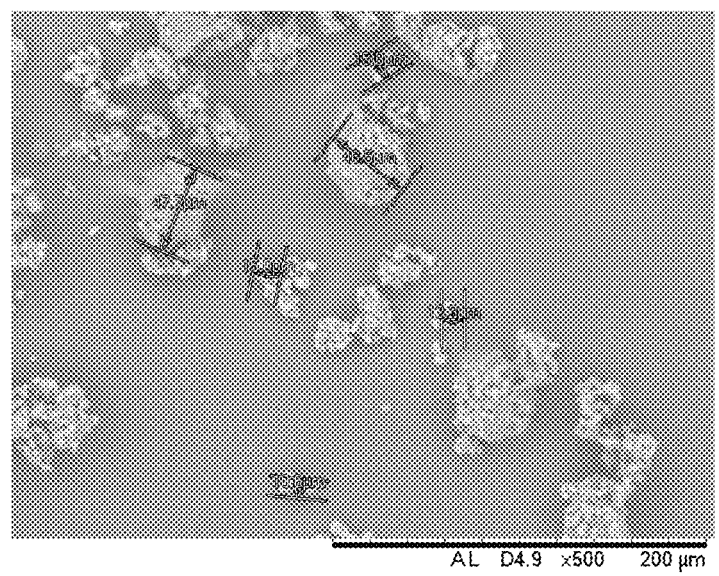
FIG. 2 shows the morphology of microparticles as observed by scanning electronic microscope.

B) Characterization of Photo Crosslinked Particles:

Particle size distribution for above mentioned four formulations (Table 1) is presented in Table 6. Photo crosslinked films could be easily grinded when ball mill was frozen using liquid nitrogen. PEGDA 250 alone films produced particles with lower size due to more brittleness of film. Morphology of microparticles as observed by scanning electronic microscope is shown in FIG. 2. Irregular shaped particles formed after grinding in ball mill.

TABLE 6

Particle size distribution of PcMPs presented as X10 = 10% particles with size lower than value mentioned, X50 = 50% particles with size lower than value mentioned, X90 = 90% particles with size lower than value mentioned and X99 = 99% particles with size lower than value mentioned.

| | Formulation F1 | | | | | Formulation F2 | | | |
|---|---|---|---|---|---|---|---|---|---|
| X % particles | X10 | X50 | X90 | X99 | X % particles | X10 | X50 | X90 | X99 |
| Size (μm) | 40.0 | 119.0 | 155.7 | 290.7 | Size (μm) | 19.2 | 61.9 | 115.0 | 162.1 |

TABLE 6-continued

Particle size distribution of PcMPs presented as X10 = 10% particles with size lower than value mentioned, X50 = 50% particles with size lower than value mentioned, X90 = 90% particles with size lower than value mentioned and X99 = 99% particles with size lower than value mentioned.

| | Formulation F3 | | | | | Formulation F4 | | | |
|---|---|---|---|---|---|---|---|---|---|
| X % particles | X10 | X50 | X90 | X99 | X % particles | X10 | X50 | X90 | X99 |
| Size (μm) | 7.9 | 98.5 | 179.7 | 283.7 | Size (μm) | 37.4 | 132.4 | 220.8 | 343 |

Thermal analysis of PcMPs (FIG. 3) showed shift in baseline at ~260° C. indicated presence of small amount of Dexamethasone as it was dispersed in MPs.

This dispersed Dexamethasone lead to initial burst release in all formulations.

Figure 3:
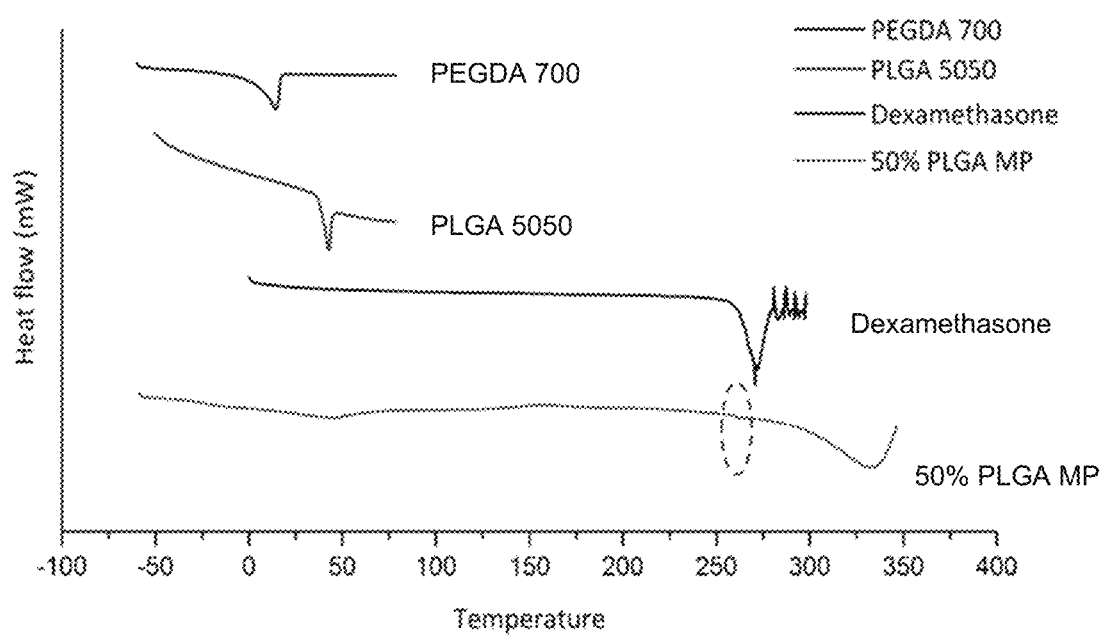
FIG. 3 illustrates DSC analysis of polymers, dexamethasone and PcMPs.

In FIG. 3, DSC curve of only one formulation (50% PLGA containing PcMPs) shown as the results for other formulations was similar.

Figure 4:
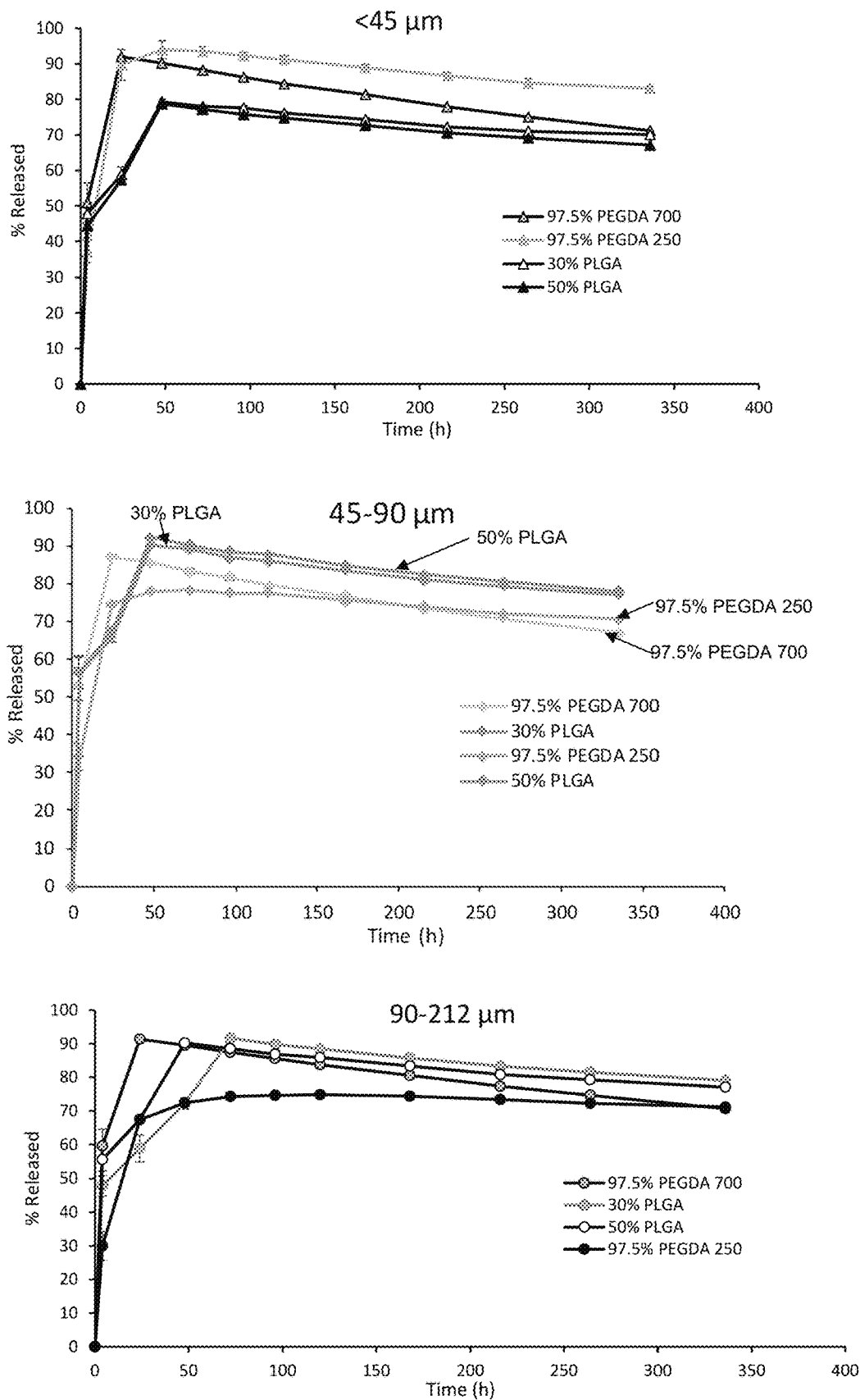
FIG. 4 illustrates in vitro release of dexamethasone from microparticles (PcMPs) with three different size ranges.

C) In Vitro Drug Release Study:

Release of DEX from different PcMPs formulations is depicted in FIG. 4.

50% PLGA sustained release but still burst effect observed due to adsorbed drug on the surface of PcMPs.

Higher PLGA content in particles below 45 μm in size sustained release, at higher sizes no significant difference was observed. However, the release can be modified by varying the formulation composition.

Figure 5:
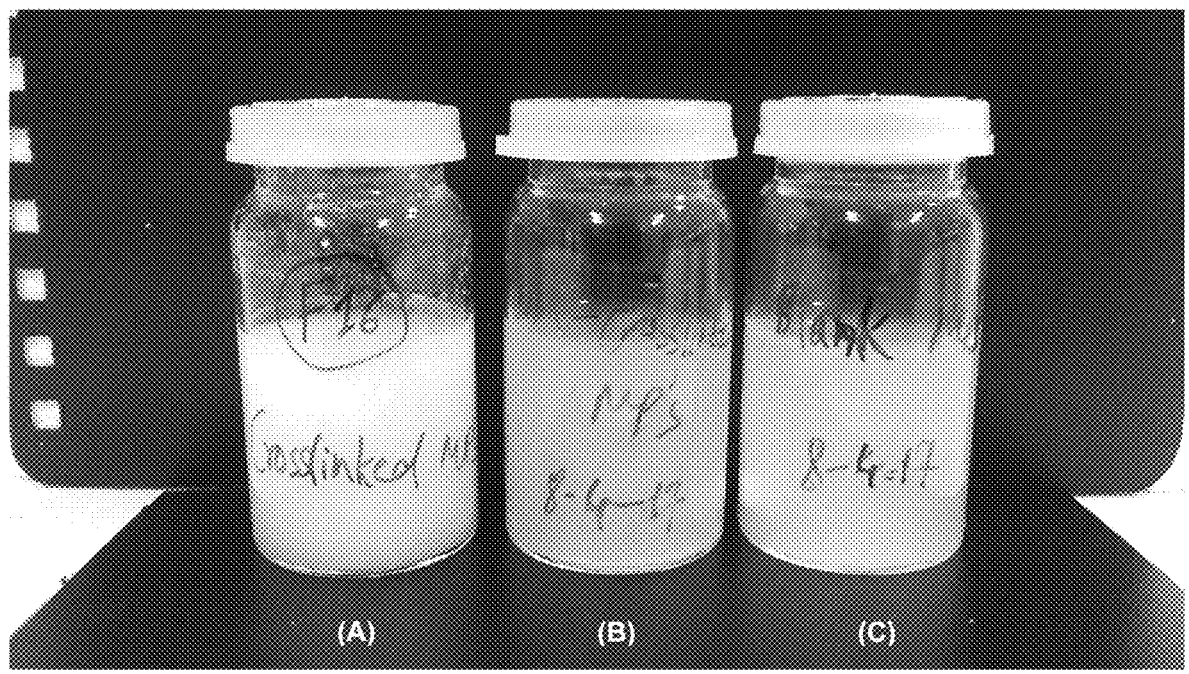
FIG. 5 shows A) Photo crosslinked particles B) Non-photo crosslinked particles and C) Blank (without dexamethasone) particles prepared with emulsification solvent evaporation method.

D) Formulation and Characterization of Photo Cross-linked Micro/Nano-Particles Using Emulsion Evaporation-Precipitation Method:

Photo crosslinked polymeric particles were obtained with high yield and as white mass whereas non-crosslinked polymeric particles were sticky and low yield obtained (FIG. 5).

Figure 6:
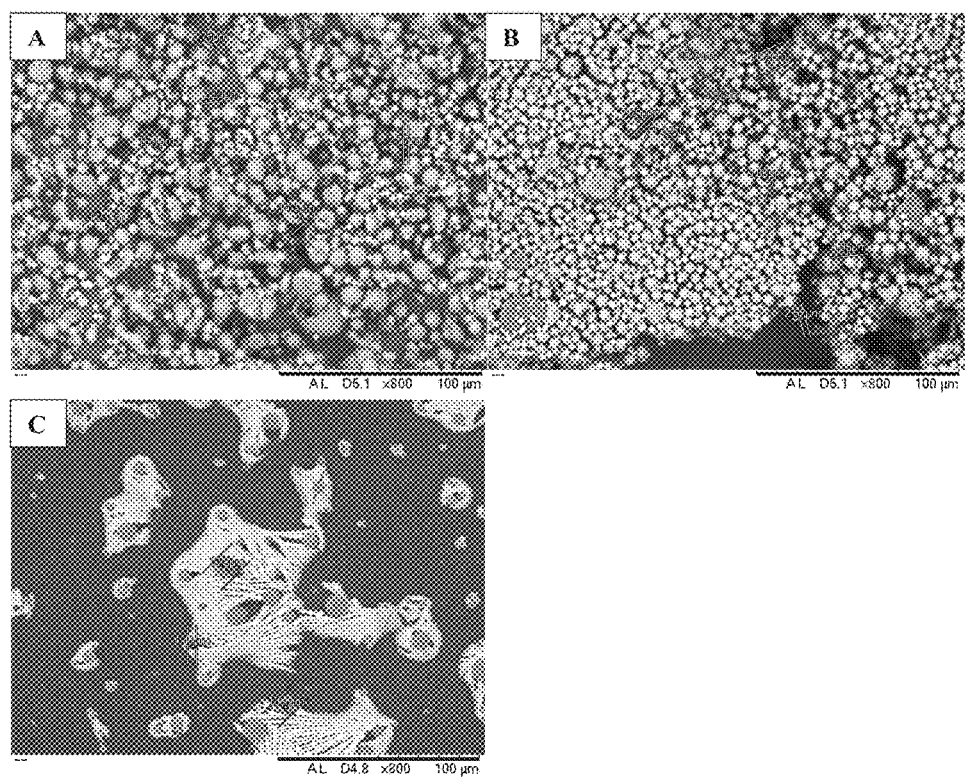
FIG. 6 shows the morphology of A) photo-crosslinked, B) non-photo crosslinked and C) blank particles analysed by scanning electronic microscope.

The particles are spherical in shape in all the formulations but the photo crosslinked particles have rough surface and relatively have larger average diameter (FIG. 6).

The prepared particles were washed and freeze dried to improve the stability and remove any traces of solvents.

The PcMPs were in the size range of 2 to 30 μm and have rough surface while non-photo crosslinked MPs are in the size range of 2 to 200 μm with smooth surface.

The yield of non-photo crosslinked particles was low as only PLGA micro particles were formed while PEGDA remained as a soluble component in PVA solution phase.

The drug encapsulation efficiency of photo-crosslinked particles was almost 92%, which ensure minimum burst effect during release and lowering of dose due to high payload of drug in particles.

Increase in homogenization speed and higher surfactant concentration lead to formation of photo crosslinked nanoparticles by this method.

The particles obtained by this method can be applied as topical formulations (eye drops) or by sub-conjunctival route for sustained delivery of drugs.

TABLE 7

Particle size distribution of photo crosslinked, non-photo crosslinked and blank PcMPs by Laser diffractometer.

| 20% PLGA, 2% DEX PcMPs (F16) | | | | | 20% PLGA, 2% DEX Non-PcMPs (F17) | | | | |
|---|---|---|---|---|---|---|---|---|---|
| X % particles | X10 | X50 | X90 | X99 | X % particles | X10 | X50 | X90 | X99 |
| Size (μm) | 2.1 | 8.5 | 19.1 | 28.6 | Size (μm) | 1.7 | 6.9 | 26.3 | 201.1 |

| 20% PLGA, Blank PcMPs (F18) | | | | | PLGA MPs (F20) | | | | |
|---|---|---|---|---|---|---|---|---|---|
| X % particles | X10 | X50 | X90 | X99 | X % particles | X10 | X50 | X90 | X99 |
| Size (μm) | 3.7 | 79.4 | 221.4 | 264.6 | Size (μm) | 1.7 | 7.0 | 17.2 | 23.9 |

E) In Vitro Release Study:

Burst release of dexamethasone from all MPs was observed due to the sudden release of drug present on the surface of MPs.

Dexamethasone release was slower from PLGA-PEGDA photo crosslinked MPs as compared to PLGA non-crosslinked MPs.

The release of dexamethasone can further be controlled by optimizing microparticles with respect to PLGA polymer type, PLGA content, and dexamethasone loading.

Figure 7:
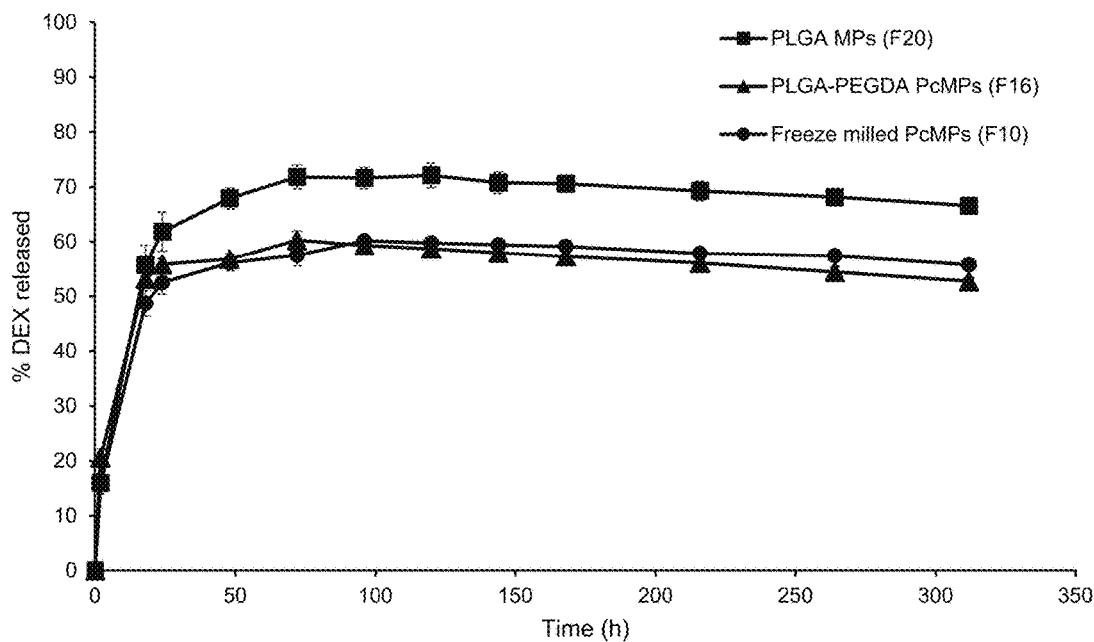
FIG. 7 illustrates in vitro release of dexamethasone from PLGA MPs, PLGA-PEGDA crosslinked microparticles (PcMPs) and milled PLGA-PEGDA PcMPs.

FIG. 7 shows In vitro release of dexamethasone from PLGA MPs, PLGA-PEGDA crosslinked microparticles (PcMPs) and milled PLGA-PEGDA PcMPs.

Figure 8:
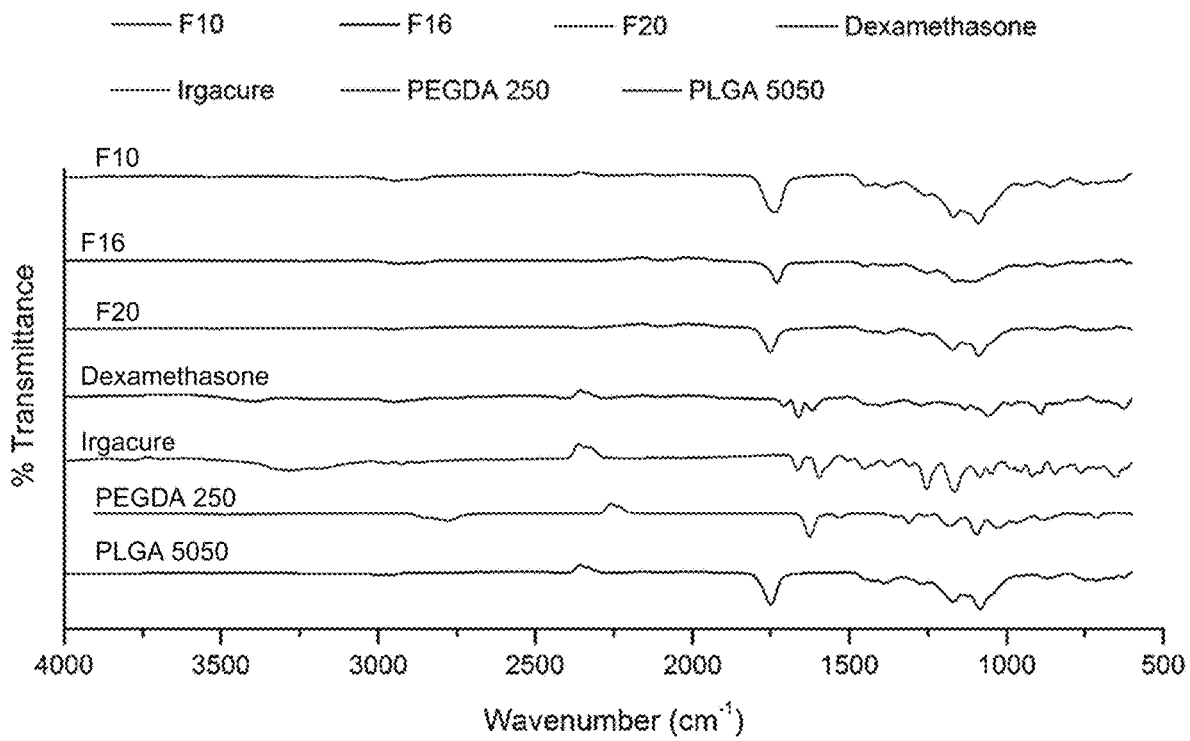
FIG. 8 shows FTIR analysis of PLGA MPs and PcMPs.

F) FTIR Analysis of PLGA MPs and PcMPs:

As shown in FIG. 8 Carbonyl —C═O peak of PLGA at ~1750 $cm^{-1}$ is prominent in PLGA non-crosslinked MPs while this peak is slightly shifted in photo crosslinked PEGDA-PLGA MPs (F10 & F16 formulations).

Strong absorption peak in PEGDA for —C═C at ~1633 $cm^{-1}$ is absent in PcMPs (F10 & F16) indicating complete cross-linking of PEGDA in these MPs.

—C—O stretching peak of PLGA at 1050-1250 $cm^{-1}$ is broadened and weak in intensity for the F16 formulation indicating partial coating of PLGA with PEGDA 250 polymer during emulsion precipitation process of formulation.

G) Optimization of PcMPs:

1. Effect of Drug Loading:

Increase in drug loading did not reduce particle size significantly, importantly particles were within our target size i.e., 30-40 µm (Table 8).

TABLE 8

Particle size distribution of 2, 5, and 10% DEX loaded PcMPs and blank PcMPs measured by Laser diffractometer.

| 20% PLGA, 2% DEX PcMPs | | | | | 20% PLGA, 5% DEX PcMPs | | | | |
|---|---|---|---|---|---|---|---|---|---|
| X % particles | X10 | X50 | X90 | X99 | X % particles | X10 | X50 | X90 | X99 |
| Size (µm) | 2.1 | 8.5 | 19.1 | 28.6 | Size (µm) | 3.9 | 18.9 | 40.4 | 50.2 |
| 20% PLGA, 10% DEX PcMPs | | | | | 20% PLGA, 10% DEX PcMPs | | | | |
| X % particles | X10 | X50 | X90 | X99 | X % particles | X10 | X50 | X90 | X99 |
| Size (µm) | 1.2 | 12.8 | 17.8 | 21.1 | Size (µm) | 5.7 | 18.3 | 96.5 | 191.9 |

Figure 9:
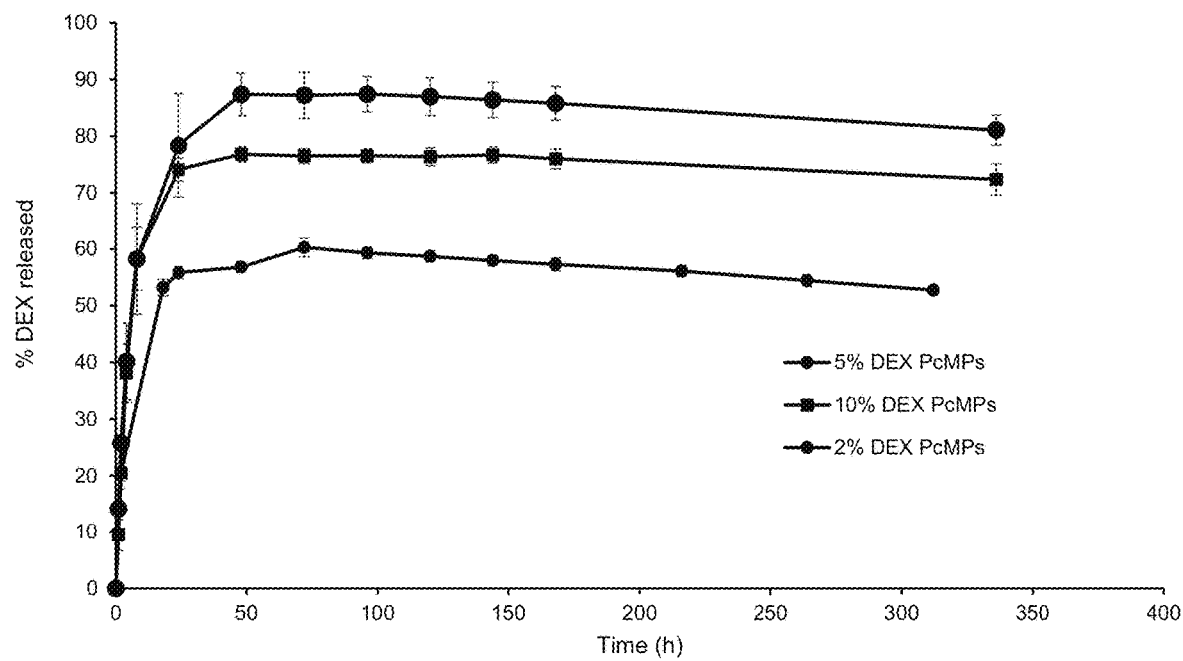
FIG. 9 illustrates in vitro release of dexamethasone from 2, 5, and 10% Dexamethasone loaded PcMPs.

In vitro release of dexamethasone from PcMPs with different drug loading is presented in FIG. 9. Higher amount of dexamethasone was released from PcMPs with 5% loading while 10% loading slower the release, might be due to poor solubility and wettability of drug.

Lower loading lead to 60% drug released which might be due to entrapment of drug into highly cross-linked polymer matrix which was not able to come out in the release medium.

5% drug loaded PcMPs release higher amount of dexamethasone and thus lower amount was trapped in polymer matrix. This formulation needs to be optimized to reduce burst effect and sustain the release.

FIG. 9 shows in vitro release of dexamethasone from 2, 5, and 10% Dexamethasone loaded PcMPs.

Due to the stability issues related to dexamethasone, triamcinolone acetonide (TA) was used as model drug in recent formulations.

Effect of photo-crosslinking time on release profile of drug (TA) was studied by preparing formulations with emulsification precipitation method, developed and optimized in this project.

Drug (TA) release study is ongoing for particles prepared with different cross-linking time PcMPs optimization is ongoing to achieve sustain release for up to 6 months.

2. Effect of Crosslinking Time:

PcMPs were prepared with same method as before and the PcMPs suspension was exposed to UV light for 5, 15, 30 and 60 min.

In vitro release of drug (TA) from these microparticles was studied as per set protocol.

Figure 10:
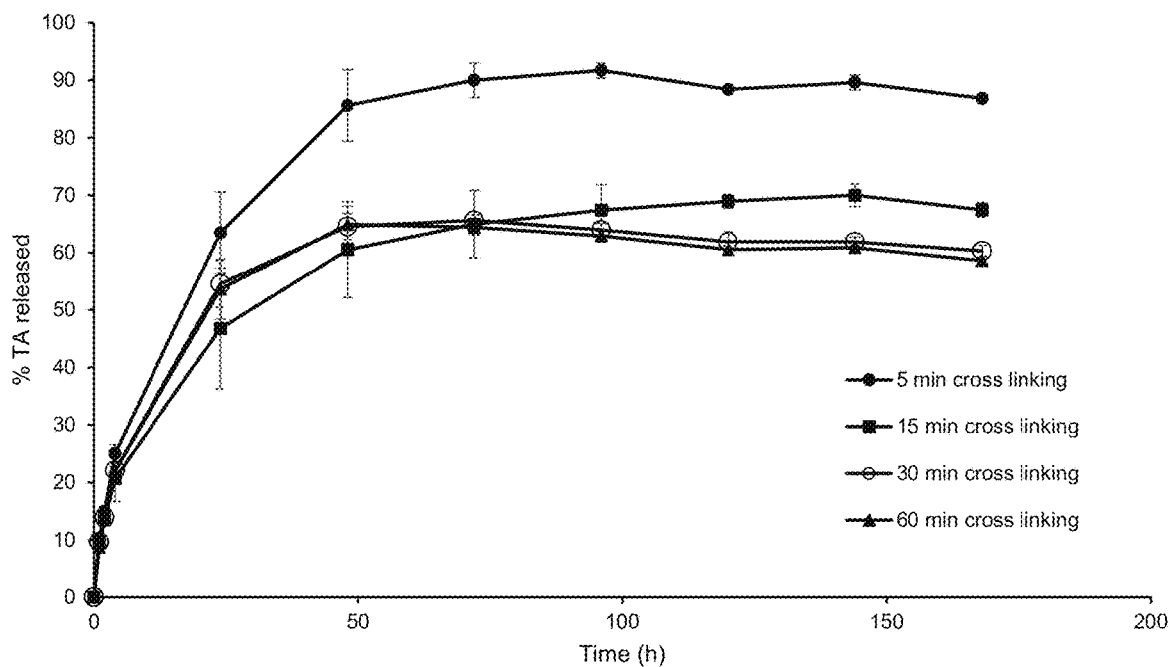
FIG. 10 illustrates in vitro release of triamcinolone acetonide (TA) from PcMPs crosslinked for 5, 15, 30 and 60 minutes.

As expected, UV crosslinking for 5 minutes released drug faster due to lower crosslinking between PEGDA polymer chains (FIG. 10).

No significant difference between 15, 30, 60 min of crosslinking time and thus 15 min of crosslinking time was considered as optimum.

FIG. 10 shows In vitro release of triamcinolone acetonide (TA) from PcMPs crosslinked for 5, 15, 30 and 60 minutes.

3. Effect of Polymer Type:

Other polymers like acid terminated PLGA 75:25, ester terminated PLGA (50:50 and 75:25 ratio), poly (ε-caprolactone), poly (L-lactide-co-caprolactone) were used to control the release.

Due to highly hydrophobic nature of poly (C-caprolactone), poly (L-lactide-co-caprolactone) polymers, 5% polyethyleneglycol (PEG, Mn=200) was used to obtain microparticles.

Figure 11:
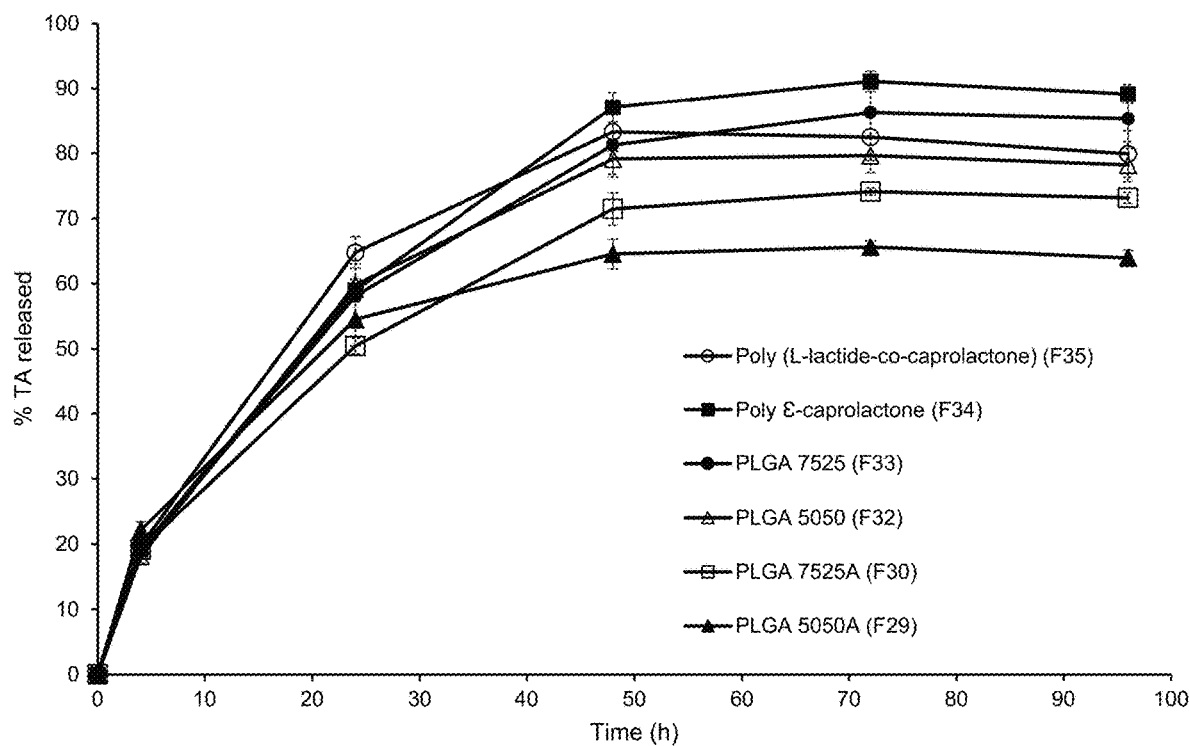
FIG. 11 illustrates in vitro release of triamcinolone acetonide (TA) from PcMPs prepared with different grades of PLGA, poly (ε-caprolactone), and poly (L-lactide-co-caprolactone).

Addition of PEG into PcMPs led to more porous microparticles and released drug faster as compared to different grades of PLGA PcMPs (F29-F33 formulations) (FIG. 11).

FIG. 11 shows In vitro release of triamcinolone acetonide (TA) from PcMPs prepared with different grades of PLGA, poly (ε-caprolactone), and poly (L-lactide-co-caprolactone).

Further optimization of PcMPs is ongoing and different polymers are explored to further sustain the release of drug from the formulation.

Stability testing of some of the PLGA PcMPs is ongoing.

Effect of sterilization method on characteristics and stability of PcMPs will be studied.

The present invention provides new micro/nano particulate formulation for sustained ocular delivery. The studies herein have developed photo-crosslinked microparticles with two different methods which are easy to scale up.

Emulsification precipitation method (FIG. 12) is an entirely novel method which also include use of novel polymer combination (PLGA-PEGDA) (described in co-pending WO2017/081154A1).

Higher encapsulation of dexamethasone/TA was achieved by this method which will ensure lowering of dose and thus ease in administration.

The studies herein have achieved sustained release of drug over period of 4 weeks and working on further sustaining release up to 6 months.

This kind of formulation even with 2-3 weeks of sustained release can be used to deliver steroids and antibiotics in post-cataract treatments.

Optimised formulations will be tested for ocular compatibility and pharmacokinetic study.

The invention claimed is:

1. A method of making a nanoparticle or microparticle ocular implant comprising
    a) 99 to 60% (w/w) of a photopolymerizable composition selected from the group consisting of fragments or monomers of polyalkylene glycol diacrylate and polyalkylene glycol dimethacrylate, wherein the photopolymerizable composition has a molecular weight in the range of 100 to 20,000 Dalton;
    b) a biodegradable polymer selected from the group consisting of lactide/glycolide co-polymer (PLGA), polylactic acid (PLA), polyglycolic acid (PGA), polycaprolactone (PCL), lactide/caprolactone copolymer (PLC), poly (L-lactide) (PLLA) and mixtures, copolymers, and block copolymers thereof;
c) a photoinitiator; and
d) a therapeutic agent,
the method comprising the steps of:
I) mixing the therapeutic agent, the photopolymerizable composition, and the biodegradable polymer, to form mixture i);
II) adding the photoinitiator to form mixture ii);
III) irradiating the mixture ii) with light at a wavelength of between 230 to 550 nm, between 300 to 525 nm, or between 350 to 490 nm for between 1 second and 60 minutes; and
IV) processing the irradiated mixture ii) to obtain particles.

2. A method as claimed in claim 1 where in the mixture ii) is cast as a film prior to irradiation and the step of processing the irradiated mixture includes milling the irradiated film to obtain photo-crosslinked microparticles.

3. A method as claimed in claim 2 wherein mixture i) is stirred between 2 minutes to 48 hours at 100 to 300 rpm.

4. A method as claimed in claim 2 wherein at least one of dichloromethane, methanol, acetone or mixture of dichloromethane:methanol is used as co-solvents and mixture i) is vortexed for 2 to 5 minutes.

5. A method as claimed in claim 2 wherein the photoinitiator is dissolved in minimum amount of solvent prior to UV exposure and wherein the solvent is chosen from acetone, absolute alcohol, or methanol.

6. A method as claimed in claim 2 wherein the film has a thickness of 0.2 to 1 mm.

7. A method as claimed in claim 2 wherein the film is exposed to UV light for 48 to 300 sec. at 93 to 100% intensity of UV lamp.

8. A method as claimed in claim 2 wherein the formed films are ground in a ball mill or freeze mill using liquid nitrogen.

9. A method as claimed in claim 2 wherein the photo-crosslinked particles obtained can be separated into different sizes and size ranges as required.

10. A method as claimed in claim 1 wherein the mixture ii) is homogenised at high speed prior to irradiation to form an emulsion and photo-crosslinked particles are obtained by solvent extraction post irradiation.

11. A method as claimed in claim 10 wherein the mixture i) contains between 5 to 30% PLGA polymer and between 93.5 to 64% photopolymerizable polymer (PEGDA) of total excipient/polymer content prior to addition of the therapeutic agent.

12. A method as claimed in claim 10 wherein the mixture i) is dissolved in 0.2 to 2 ml acetone, methanol, dichloromethane, or mixture of dichloromethane and methanol.

13. A method as claimed in claim 10 wherein the mixture ii) contains 1 to 5% therapeutic agent and between 0.1 to 1% w/v photo initiator of total drug and excipient content.

14. A method as claimed in claim 10 wherein the emulsion is formed when mixture ii) added to 0.15 to 2% w/v polyvinyl alcohol (PVA) aqueous solution or 0.01 to 0.5% w/v d-α-tocopheryl polyethylene glycol 1000 succinate (vitamin E TPGS or TPGS) or 0.1 to 2% w/v polysorbate 80 (Tween 80) or 0.1 to 1% w/v Poloxamer 188 when used as emulsifiers with homogenization at speed between 6000 to 18000 rpm for between 1 to 4 min to reduce size to micro or nanometer range.

15. A method as claimed in claim 10 wherein the emulsion is added to between 5 to 20 mL of 50 to 500 mM sodium sulfate solution with homogenization at speed between 6000 to 18000 rpm for between 1 to 4 min to reduce size to micro or nanometer range and/or precipitate the PEGDA on the surface of PLGA particles.

16. A method as claimed in claim 10 wherein the emulsion is stirred at 100 to 400 rpm and simultaneously exposed to UV light at a wavelength of 230 to 380 nm for 2 to 6 min.

17. A method as claimed in claim 10 wherein solvent evaporation is performed by stirring the emulsion at around 50 to 200 rpm for 24 to 72 hr.

18. A method as claimed in claim 10 wherein micro or nanoparticles are collected and washed to remove excess excipients.

19. A method as claimed in claim 10 wherein micro or nanoparticles formed can further be coated with mucoadhesive polymers selected from the group consisting of chitosan, sodium alginate, sodium hyaluronate, sodium carboxymethylcellulose or thiolated polymers selected from the group consisting of chitosan-cysteine, chitosan-thiobutylamidine, poly(acrylic acid)-cysteine, poly(acrylic acid)-cysteamine, carboxymethylcellulose-cysteine, and alginate-cysteine to improve the retention time in the ocular tissue.

20. A method as claimed in claim 1 wherein the mixture ii) is subjected to microfluidic apparatus to and irradiated to obtain photo-crosslinked particles.

21. A method as claimed in claim 1 wherein the mixture ii) is subjected to electrospraying and irradiated to obtain photo-crosslinked particles.

\* \* \* \* \*